United States Patent
Saarinen et al.

(10) Patent No.: US 11,793,487 B2
(45) Date of Patent: Oct. 24, 2023

(54) TRANSDUCER ARRAY DEVICE, METHOD AND SYSTEM FOR CARDIAC CONDITIONS

(71) Applicants: Annamarie Saarinen, North Oaks, MN (US); Paul Saarinen, North Oaks, MN (US)

(72) Inventors: Annamarie Saarinen, North Oaks, MN (US); Paul Saarinen, North Oaks, MN (US)

( * ) Notice: Subject to any disclaimer, the term of this patent is extended or adjusted under 35 U.S.C. 154(b) by 559 days.

(21) Appl. No.: 15/416,634

(22) Filed: Jan. 26, 2017

(65) Prior Publication Data

US 2018/0206819 A1    Jul. 26, 2018

(51) Int. Cl.
*A61B 8/00*    (2006.01)
*A61B 8/08*    (2006.01)

(52) U.S. Cl.
CPC .......... *A61B 8/4444* (2013.01); *A61B 8/0866* (2013.01); *A61B 8/4227* (2013.01); *A61B 8/5207* (2013.01); *A61B 8/0883* (2013.01); *A61B 8/4488* (2013.01); *A61B 8/461* (2013.01)

(58) Field of Classification Search
CPC .................................................... A61B 8/4444
See application file for complete search history.

(56) References Cited

U.S. PATENT DOCUMENTS

| | | | | |
|---|---|---|---|---|
| 4,222,274 A | * | 9/1980 | Johnson ................. | A61B 8/406 128/915 |
| 4,348,904 A | * | 9/1982 | Bautista, Jr. ........... | G10K 11/02 310/334 |
| 5,297,553 A | * | 3/1994 | Sliwa, Jr. .............. | B06B 1/0674 29/25.35 |
| 5,562,096 A | * | 10/1996 | Hossack .................. | A61B 8/12 600/446 |
| 5,656,016 A | * | 8/1997 | Ogden .................. | A61M 37/00 601/2 |
| 5,957,850 A | * | 9/1999 | Marian, Jr. .............. | A61B 8/12 29/25.35 |
| 6,019,725 A | * | 2/2000 | Vesely ................. | A61B 8/0841 600/447 |
| 6,183,578 B1 | * | 2/2001 | Ritter .................... | B06B 1/0611 156/155 |

(Continued)

OTHER PUBLICATIONS

Gerda Meijler, Cranial Ultrasonography: Technical Aspects, Neonatal Cranial Ultrasonography, DOI 10.1007/978-3-642-21320-5_2, 2012, p. 7-14 Springer-Verlag Berlin Heidelberg.

(Continued)

*Primary Examiner* — Pascal M Bui Pho
*Assistant Examiner* — John Denny Li
(74) *Attorney, Agent, or Firm* — Thorpe North & Western, LLP; Jed H. Hansen

(57) ABSTRACT

Techniques of this disclosure are for a transducer array device, method and system. An ultrasound wrap for securing an array of piezoelectric transducers at a thoracic cavity anterior for echocardiology imaging, the ultrasound wrap including a transducer portion having an array of piezoelectric transducers mounted to an inner concave surface of a semi-rigid structure, and a securing portion extending from the transducer portion and comprising flexible material securely fitting around the thorax of a patient limiting the movement of the transducer portion.

19 Claims, 5 Drawing Sheets

(56) References Cited

U.S. PATENT DOCUMENTS

| | | | | |
|---|---|---|---|---|
| 6,482,158 B2 * | 11/2002 | Mault | ............... | A61B 5/044 600/437 |
| 8,038,622 B2 * | 10/2011 | Abraham | ............... | A61B 8/565 600/459 |
| 9,326,553 B1 * | 5/2016 | Ross | ............... | A41C 3/0064 |
| 9,579,055 B1 * | 2/2017 | Rood | ............... | A61B 5/0444 |
| 2002/0151790 A1 * | 10/2002 | Abend | ............... | A61B 8/06 600/437 |
| 2002/0188198 A1 * | 12/2002 | Hong | ............... | A61B 8/4494 600/437 |
| 2004/0167409 A1 * | 8/2004 | Lo | ............... | A61B 5/02438 600/485 |
| 2005/0020918 A1 * | 1/2005 | Wilk | ............... | A61B 8/483 600/439 |
| 2005/0124897 A1 * | 6/2005 | Chopra | ............... | A61B 8/0808 600/459 |
| 2005/0228281 A1 * | 10/2005 | Nefos | ............... | A61B 8/08 600/446 |
| 2006/0100530 A1 * | 5/2006 | Kliot | ............... | A61B 5/0002 600/483 |
| 2007/0078345 A1 * | 4/2007 | Mo | ............... | A61B 8/12 600/459 |
| 2007/0293781 A1 * | 12/2007 | Sims | ............... | A61B 5/1135 600/534 |
| 2011/0077526 A1 * | 3/2011 | Zwirn | ............... | A61B 5/0095 600/459 |
| 2011/0125026 A1 * | 5/2011 | Neto | ............... | A61B 8/06 600/463 |
| 2012/0035426 A1 * | 2/2012 | Mielcarz | ............... | A61B 5/0015 600/300 |
| 2012/0065479 A1 | 3/2012 | Lahiji et al. | | |
| 2012/0232398 A1 | 9/2012 | Roham et al. | | |
| 2012/0277640 A1 * | 11/2012 | Lewis, Jr. | ............... | A61B 8/4227 601/2 |
| 2013/0267850 A1 * | 10/2013 | Berman | ............... | A61B 8/466 600/443 |
| 2014/0081144 A1 * | 3/2014 | Moehring | ............... | A61B 5/725 600/454 |
| 2014/0336483 A1 * | 11/2014 | Abee | ............... | A61B 5/14552 600/323 |
| 2015/0133788 A1 * | 5/2015 | Mauldin, Jr. | ............... | A61B 8/4281 600/444 |
| 2015/0158052 A1 * | 6/2015 | Latev | ............... | H01L 41/0475 310/316.01 |
| 2016/0243381 A1 * | 8/2016 | Alford | ............... | A61N 7/00 |
| 2017/0080255 A1 * | 3/2017 | Law | ............... | G01S 7/521 |
| 2017/0112476 A1 * | 4/2017 | Belevich | ............... | A61B 8/4494 |
| 2017/0319179 A1 * | 11/2017 | Kandori | ............... | A61B 8/5269 |
| 2019/0046158 A1 * | 2/2019 | Kroon | ............... | A61B 8/4245 |

OTHER PUBLICATIONS

Rebecca Snider, et al. Two-Dimensional Echocardiographic Determination of Aortic and Pulmonary Artery Sizes from Infancy to Adulthood in Normal Subjects, The American Journal of Cardiology; Jan. 1, 1984; p. 218-224; vol. 53; USA.

Qian-Jing Hu, et al.; Diagnostic performance of lung ultrasound in the diagnosis of pneumonia; a bivariate meta-analysis; Int J. Clin Exp Med 2014; 7(1); 115-121; www.ihcem.com/ISSN:1940-5901/UCEM.1310043; Oct. 31, 2013 Department of Respiratory and Critical Care Medicine, West China Hospital of Sichuan University and Division of Pulmonary Disease, State Key Laboratory of Biotherapy of China, Chengdu 610041, China.

* cited by examiner

TRANSDUCER ARRAY DEVICE, METHOD AND SYSTEM FOR CARDIAC CONDITIONS

The present invention relates generally to electronic imaging, particularly to a device, method, and system for ultrasonic diagnostics of patients.

BACKGROUND

Ultrasound, which is an oscillating sound pressure wave, has applications in many different fields. For example, ultrasonic systems are used to detect objects and measure distances and ultrasonic imaging is used in medicine to produce images of, for example subject's internal organs, such as a heart. Ultrasound is used in echocardiograms ("echos") to image the heart, particularly structure and flow. In addition to medical applications, ultrasound imaging is used in product quality testing to detect flaws.

Ultrasound imaging is preferred in medicine because of its relative low cost and radiation-free operation. Portable handheld ultrasound systems that provide greater access to ultrasound diagnostic techniques have become available. Diagnostic ultrasound equipment includes a probe with transducers or a patch that includes an array of transducers. The portability of the equipment has allowed medical personnel to use this equipment in the screening of patients for health conditions or physical defects, particularly in rural locations. The images acquired are interpreted by a physician or trained medical personnel at the imaging site or are sent to an off-site location for analysis. Staffing clinics to acquire images and screen patients in rural, third world, or low income areas can often be difficult. Additionally, sending images to a network for later analysis by trained personnel can often take time, and this delay, in some cardiac defect conditions, can be fatal.

Trained personnel are particularly necessary in acquiring images for newborns for at least two reasons. First, there are technical challenges associated with obtaining these images. Most ultrasound systems are designed to image large cooperative patients such as adults. Imaging newborn babies, infants and young children is more difficult requiring alteration of transducer frequency and size, and requiring a technician to compensate for a child's movement, more rapid respiration and heartbeat, and lack of cooperation. More importantly, most screens in adult echocardiography assume that cardiac position and anatomy are within a range of normal, however, in the newborn population, there is a high incidence of congenital heart disease, cardiac malposition, and transitional cardiac anatomy and physiology that requires an even higher level of skilled acquisition to recognize and interrogate these defects appropriately. Most pediatric echo cardiographers have training even beyond that of their adult counterparts due to the technical challenges and the complexity of the cardiac diagnoses they encounter.

DESCRIPTION

Screening patients with portable ultrasound imaging has advanced medicine and has saved lives. Aspects of this disclosure discuss transducer arrays in equipment that improves ease of use and improves consistency of image quality and clarity, so that people without training, or little training, may operate the equipment and obtain useful images. The improved ultrasound equipment of this disclosure may allow more people to use the equipment, and consequently, allow image acquisition in areas of the world that do not have enough highly trained ultrasound imaging professionals that are able to image newborn hearts. For example, people in rural locations or third world countries may not have access to ultrasound imaging equipment or training for reading images, but they may be able to use the equipment of this disclosure to acquire an interpretable ultrasound image. Improving access to ultrasound imaging may also increase the medical data on newborn cardiac conditions and allow screening for cardiac defects and a viable diagnostic tool for other medical conditions in underdeveloped countries.

Aspects of the invention disclose utilizing a transducer array, or a plurality of transducer arrays, that a user may easily place at the correct location of the chest and the user does not have to move the transducer array after placement in an optimal imaging location and secured. The shape of the piece that holds the transducer arrays has a curved concave shape that conforms to the left anterior thorax of a newborn or small child, allowing the transducers to be in direct contact with the newborn's skin at the left anterior chest wall near the heart. The concave portion may be made of a rigid or semi-rigid material, allowing some flexing, but remaining stable by limiting the movement of the transducers. The transducer arrays on the semi-rigid concave portion may be part of a wrap, which secures around the thorax of the newborn and securing the transducer arrays against the skin, so that imaging may occur without disturbing or causing discomfort and through limited movement of the transducer array quality improves. The easy to use equipment simplifies placement without sacrificing image quality.

In another aspect of the disclosure, the invention may disclose using the transducer array design with computer automated imaging to automatically image, so that users with little to no training may be able to obtain good ultrasound images. In other aspects, the disclosure may include networks for possible automated detection of cardiac defects. With increased volume of images acquired during wider spread screening by untrained personnel, image analysis by trained professionals is increasingly important to analyze the image and detect defects or conditions in newborns that untrained (or under trained) personnel may not recognize during imaging. Computer networks may allow image reading by trained professionals to occur either onsite at the location of image acquisition or to be sent offsite to a location with medical professionals (e.g., doctors, technicians, or trained image readers) who may access the images for reading and further analysis.

Computer networks allow us to collect and store greater amounts of data, i.e. echocardiograms, and may improve access by trained medical personnel to the images. However, because of the increased volume of data collection with the ability of wider spread ultrasound imaging for newborn heart screening, computer networks have increased delays in image analysis and potential defect detection. Although computer networks have improved access of images by professionals, computer networks have not increased the number of necessary trained readers to address the increase in images needing to be read quickly to identify life threatening heart defects in newborns that need immediate medical treatment. Thus, computer networks may increase delays in image analysis and defect detection, and in some situations, may cause a fatal delay for a newborn with a heart defect that may have been prevented had the defect been identified sooner, giving the newborn sufficient time to get the necessary medical attention. Aspects of the invention are necessarily rooted in computer technology to overcome a problem specifically arising in the realm of computer networks. Some aspects of this disclosure may improve the time of cardiac defect detection in newborns by using simple to use transducer arrays and by using computing devices to automatically detect a potential defect. Automation of the newborn's heart condition by the computing device reduces that need for trained professionals both onsite and offsite to identify a potential heart condition. Instead, detection of a heart condition occurs during image acquisition, so that critical time is not lost.

In other aspects of this disclosure, the computing device may reduce the volume of images that are sent to trained medical professionals for analysis. Instead of sending all newborn heart images, including those of healthy newborns and those with heart defects, the computing device may only send those with potential heart conditions greatly reduces the volume of images that may need further analysis by medical professionals. Medical professionals can then spend time with further diagnosis and treatment planning, rather than spending time reviewing healthy images during screening for defects. By using an easy to use transducer array wrap that can increase the number of newborns screened, even in rural areas, and by automating detection of infant cardiac defects with a computing device, that may also reduce the images needing to be read by trained professionals, newborns may receive critical medical treatment in a shorter period of time that may be lifesaving.

Newborns and infants with critical congenital heart defects may only survive a few hours or days without immediate medical attention, and due to this short window of treatment, there is less medical data collected on newborn heart conditions. Thus, increasing newborn heart defect screening may increase the data that may be useful in better understanding newborn heart conditions, as well as the number of identifiers that may indicate a potential heart condition in newborns. Further, children being identified with rheumatic heart disease may benefit from image automation with easy to use equipment that reduces or eliminates the need for highly trained and licensed operator, so that an average person may use the equipment with little training. Computing devices may be further updated and improved to identify automatically additional indications of potential heart conditions. With the increase in data and improvements to equipment that diagnoses heart defects and other cardiac conditions, survivors of heart conditions may consequently increase.

The present disclosure describes aspects of increasing screening for heart conditions in newborns by improving equipment used during screening, and allowing untrained professionals to use the equipment to acquire echo images of newborn hearts. The semi-rigid conforming concave transducer wrap may allow untrained people to image newborn babies, infants and young children in rural areas without requiring alteration of transducer frequency and size, and requiring a technician to compensate for a child's movement, more rapid respiration and heartbeat, particularly when the newborn is not cooperating. Thus, screening may occur in developing countries that may not have trained professionals readily available for imaging a newborn baby or infant. Other aspects of the present disclosure may manage the increased volume of images acquired during screening due to wider spread newborn heart screening. For example, a computing device may identify a potential heart defect at the time of screening. Immediate identification of potential heart defects eliminates the time it takes to send the image to a trained professional the time for determination of a potential defect. Additionally, instead of sending large amounts of screened infant data, including both healthy newborns and newborns with potential life-threatening heart defects, a computing device may reduce time delays by sending only those images of potential heart defects or cardiac conditions for further analysis by trained professional. Consequently, a child with a critical heart condition may be quickly identified and may then seek immediate treatment for the potentially fatal condition. This disclosure of improving the equipment for image acquisition and reducing the skill required to use the equipment quality of image acquisition of newborn and pediatric hearts and then automating defect detection of the heart overcomes the problem created by using computer networks for sharing images for further analysis of heart defect detection. The system may send ultrasound images that may contain heart defects, so that images sent for further attention by medical professionals may focus on those patients needing immediate cardiac care, and using filtering techniques may reduce the volume of overall data sent to a computer network. Trained medical professionals receiving the filtered data then may focus on confirming heart conditions and immediate treatment, instead of analyzing increased volumes of images.

The details of one or more examples are set forth in the accompanying drawings and the description below. Other features and/or advantages will be apparent from the description and drawings, and from the claims.

DETAILED DESCRIPTION

Figure 1A:
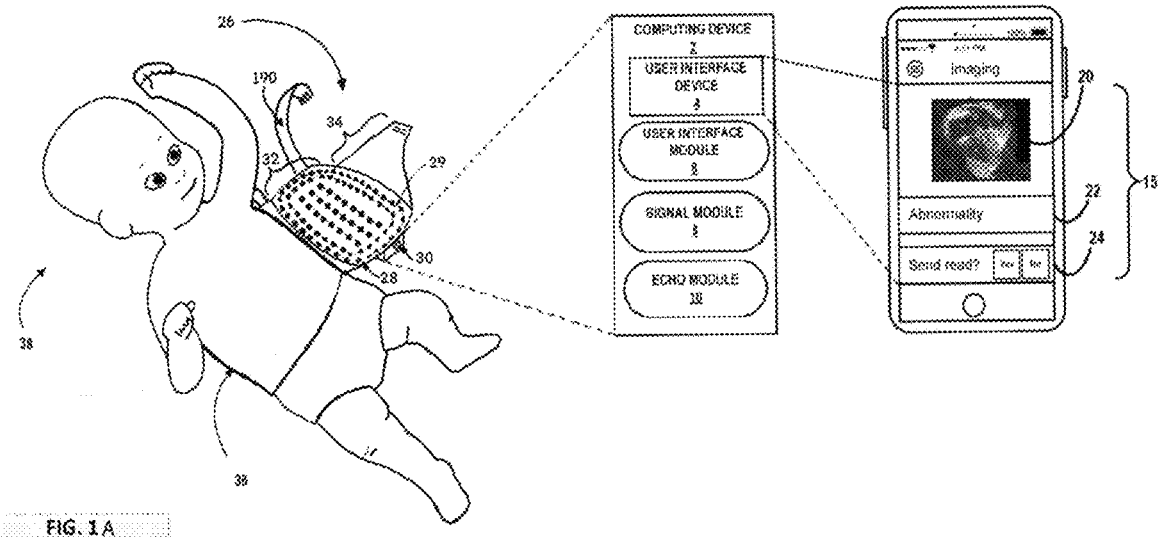
FIG. 1 includes FIG. 1A, which is a conceptual diagram illustrating an example of a transducer array device coupled to a computing device configured to execute one or more heart imaging techniques, in accordance with one or more aspects of the present disclosure.
FIG. 1B, which is a conceptual diagram illustrating an example of a transducer array device coupled to a computing device with the wrap closed around the patient.

In general, this disclosure is directed to techniques for improving echocardiograms, specifically the transducer arrays and automating identification of potential heart used in detecting and diagnosing conditions of newborn babies, infants and children. The higher level of training to use ultrasound equipment during an echocardiogram screening may make it difficult for people in remote or underdeveloped locations to screen for heart defects or heart disease. Without adequate training, the user may not know what to image or how to get a clear image at the correct angle of the heart. It is difficult for a user of the imaging equipment that does not have adequate training and knowledge to review an echo image, and from the image, be able to identify a potential heart condition. Large number of heart conditions and identifiers of each of the heart conditions may make it more difficult and time consuming for a user to analyze the image and identify as many physical attributes associated with a medical condition and select a possible specific medical condition from all cardiac conditions in newborns. For example, few trained medical echo cardiographer personnel work in rural or remote locations, and if they do, the equipment is usually too expensive to supply to these remote locations. If there is a trained user, such as a nurse in a remote village, the nurse may screen thirty newborns with ultrasound imaging and then sends the images of each of the thirty newborns to a pediatric cardiologist a few hours away for analysis. The image reader must search through each image carefully looking for any and all abnormalities that may indicate a heart condition in each image and determine what, if any, heart conditions are associated with the group of found indicators, and after spending much time searching through all of the thirty images, may then actually be able to address the child with a potentially deadly heart condition. The additional time and steps required may delay critical medical treatment and may prevent medical treatment in certain areas of the world.

In accordance with techniques of the present disclosure, the transducer portion may include one or more transducer arrays that secure to, attach to, or mount on a hard form of rigid or semi-rigid material. The transducer arrays directly be on the semi-rigid material or on a material, such as a mesh material, fixed, glued or by other techniques secured to the semi-rigid material. The semi-rigid (or rigid) material may have a shell-like shape, rectangular, oval, or other form that covers the child's left anterior thorax, near the left rib cage. The shape of the molded piece has a curve similar to the natural shape of the human left anterior side of the thorax of a child. The user may place the molded form on the child's skin over the rib cage on the left ventral side of the thorax, positioning the device near proximity to the heart. The hard material of the form limit the movement of the transducer arrays on the form and allow for a better image quality and easier, less complicated processing of the image. Once positioned in the correct area of the thorax, the user may secure the shell in place tightly against the child's skin at the outer chest wall with a wrap. The wrap securely may hold the transducer portion in place and restricts movement of the transducer arrays if the child moves. The child may be left wrapped securely for short or extended periods of time depending on the imaging needs. The transducer arrays are connected to a connection unit that may process the signals acquired from the transducer array of the wrap device, or may send the signals either wirelessly or via a cable to a computing device. The connection shell may then send the signals to a computing device automatically for further analysis.

Other aspects of the disclosure may include the transducer array receive instructions or an indication from the computing device to reimage the baby, and in some examples, the computing device may control the transducer arrays directly during signal acquisition. For example, the computing device may power one array at a time or all arrays simultaneously depending on the determination of the computing device. In other examples, the computing device may control the frequency of the transducer arrays or each crystal of the transducer array. The form of the device enable more people to acquire echo images without significant training, and the computing device may automatically control the transducer array device and determine which potential medical conditions a newborn most likely has and to present any those conditions to the user. By using a transducer array that requires little training and creates readable cardiac images, and coupling the array to a computing device that automates identification of potential cardiac issues, techniques of this disclosure may enable a user to more easily and more successfully image a child's heart and more quickly identify any potential abnormalities.

Techniques of this disclosure may provide one or more advantages. For example, by using a transducer array that is simple to use with little training and automatically image, identify and determine a potential heart condition or cardiac abnormality, techniques of this disclosure may reduce the amount of time required to diagnose newborns. Techniques of this disclosure may improve diagnosis of newborn heart conditions by "learning" identifiers of abnormalities over time, e.g., by analyzing the identifiers in the image and previous heart condition diagnosis. By making imaging equipment easier to use and intelligently automating diagnosis for the user, techniques of this disclosure may allow more untrained people to help with newborn screening for congenital heart disease and improve healthcare to newborns through early detection of critical heart conditions and improve survival rates in newborns and children with potentially fatal heart conditions, as well as on-going follow-up and treatment after diagnosis of a heart condition.

Figure 1B:
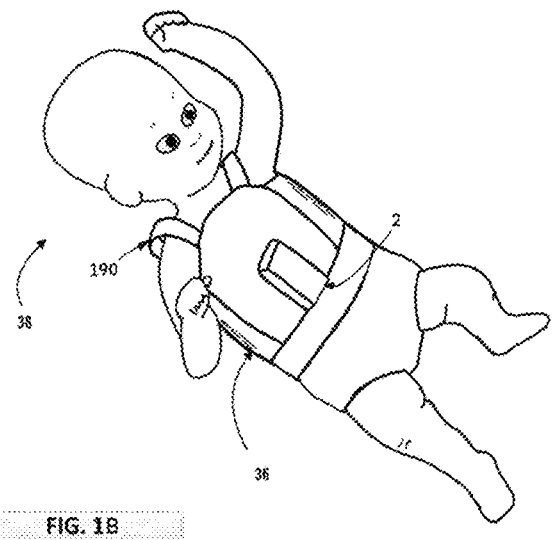

FIG. 1 is a conceptual diagram illustrating an example of a transducer array device coupled to a computing device configured to execute one or more heart imaging and diagnosis techniques, in accordance with one or more aspects of the present disclosure. FIG. 1 includes FIG. 1A, which illustrates the ultrasound cardiology imaging device wrap open and an expanded view of computing device 2. The computing device may execute one or more of automated heart imaging programs, in accordance with one or more aspects of the present disclosure. In some examples, computing device 2 may be associated with a transducer array during imaging of a child, such as baby 38. The coupling between computing device 2 may and the transducer arrays 28 is a communication coupling of electronic signals and data transfer. Computing device 2 may be integrated as part of a transducer array device (i.e., located within transducer portion 32) or communicating with transducer arrays 28 via wire or wirelessly. The user of a computing device 2 may interact with computing device 2 by providing various user inputs into computing device 2 at a graphical user interface (GUI) 15. FIG. 1 may also include FIG. 1B, which illustrates the ultrasound cardiology imaging device wrap closed, with computing device 2 attached to the outside surface.

Examples of computing device 2 may include, but are not limited to, portable or mobile devices such as mobile phones (including smartphones), laptop computers, desktop computers, tablet computers, smart television platform, personal digital assistants (PDAs), servers, mainframes, etc. As shown in the example of FIG. 1, computing device 2 may be a tablet or smartphone computer. Computing device 2, in some examples, can include user interface ("UI") device 4, UI module 6, signal receiver module 8, and echo module 10. Other modules may also be included that are not shown in FIG. 1, such as a scan module 58 of FIG. 2.

Transducer portion 32 may include a transducer array 28, or in some examples multiple transducer arrays 28. Each array contains multiple piezoelectric crystals (e.g. made with titanate ceramic or quartz) that both emit and receive ultrasound waves. The frequency of the transducer is related to the nature and thickness of the crystal. In some examples, each of transducer arrays 28 has a plurality of piezoelectric crystals that each have a distance of 1-4 mm apart from another crystal of the array. In some examples, the distance between crystals is irregular causing crystal density to vary. In other examples, each crystal of the array has uniform spacing between the crystals throughout the array. Each transducer array may be equally spaced from the array next to it, or the array spacing may vary to cause higher density in certain imaging regions. In some examples, the arrays may have a linear configuration where the crystals align along an axis, which make a trapezoidal configuration when multiple are placed next to each other. In other configurations, the arrays may have a radial configuration. Most medical ultrasound devices use soundwaves in the range of 0.5-20 MHz. Frequency determination is necessary for optimal image resolution. High-frequency waves are more attenuated than lower frequency waves for a given distance, and thus good for superficial imaging. Low-frequency waves (long wavelength) offer images of lower resolution, but can penetrate to deeper structures due to a lower degree of attenuation, so lower frequency transducers are better for going deeper into the thorax and imaging the heart. In one example, the crystals of transducer arrays 28 may have a frequency between 1-10 MHz. The frequency used, however, may depend on the size of the person being imaged and the density of their bones and tissue. For very small infants with small heads a frequency of 10 MHz may be proper, and older infants may require a frequency of 5 MHz. In FIG. 1, the newborn may be small with lower bone and tissue density common to newborns, and the transducers may use a multi-frequency (5-10 MHz) or several transducers scanning at different frequencies (5, 7.5, and 10 MHz) for providing good image resolution of readable quality. In some examples, image quality and resolution may improve using other known techniques using transducer array crystals.

Figure 2:
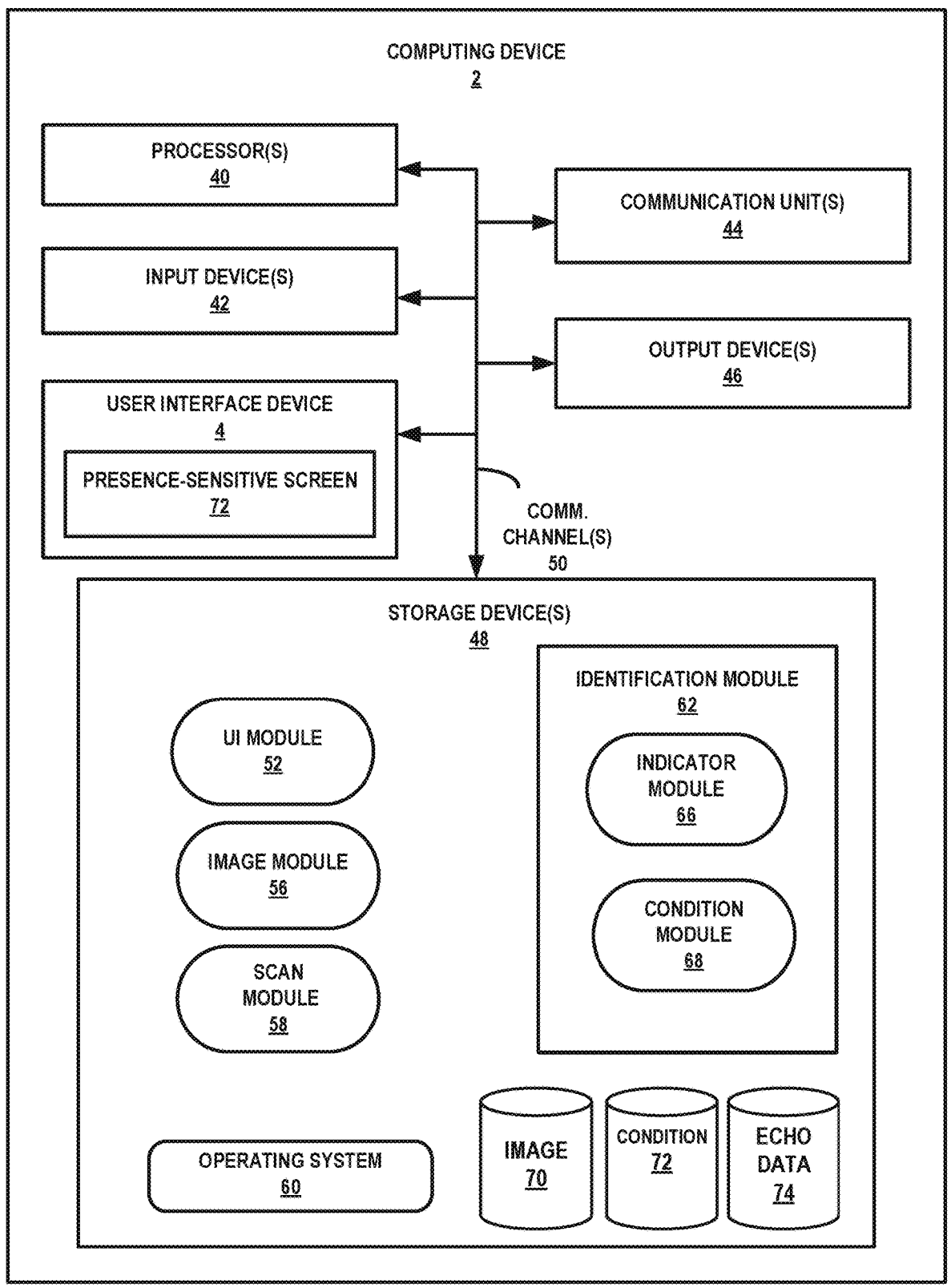
FIG. 2 is a block diagram illustrating an example of a computing device for use in echocardiography, in accordance with one or more aspects of the present disclosure.

The crystals of each array are connected by a wire, such as wire 29 that is dotted in FIG. 1. The dotting in FIG. 2 represents that the wiring may or may not be visible. The wire may carry electrical current for powering each crystal in the array and may carry signal data from the transducers crystals to and from connector unit 30. Each array of piezoelectric transducer arrays 28 includes multiple crystals that are wired together. Each array group of piezoelectric transducers 28 may simultaneously receive power from a power source, which connects to connector unit 30. The wire may carry electrical current for powering each crystal in the array and may carry signal data from the transducers crystals to and from connector unit 30. In some examples, transducer portion 32 may include multiple transducer arrays, and each array contains multiple crystals, such as piezoelectric crystals (e.g. made with titanate ceramic or quartz). In some examples, all the transducer arrays may connect with a single wire, e.g. wire 29, further connecting to connector unit 30 allowing powering and signal transfer. In other examples, each array of transducer arrays 28 may individually connect via wire to connector unit 30, allowing each array to individually be excited and send signals to connector unit 30. Individual connections allow individual excitation of the arrays and imaging control. In these examples, the transducer arrays 28 may communicate with computing device 2, for example, send signals back and forth from computing device 2 via connector unit 30. Connector unit 30, in some examples, may include the USB connector port or may send the signals from transducer arrays 28 to computing device 2 and in other examples may communicate wirelessly with transducer arrays 28, as described herein. In some examples, connector unit 30 may be computing device 2, such as FIG. 2 with computing device 2 features. In other examples, computing device 2 may be a separate computing device integrated on the outer surface of transducer housing 32, integrated both in communication with transducer portion 32 and physically on the outer surface. In another example of this disclosure, the singular transducer array may also mean the plural, transducer array (s). In these examples, the transducer arrays 28 may communicate with computing device 2, for example, send signals back and forth from computing device 2 via connector unit 30. In both examples, computing device 2 may use algorithms to determine the image based on signal techniques, based on either powering and signal control at the individual level or simultaneous level, and data is sent via connector unit 30. Transducer arrays 28 may have a rigid structure to secure to, so that there is little movement of the transducer crystals, and thus, improving image quality. For example, the wiring may be under a layer that holds the transducer arrays.

Transducer portion 32 includes at least one array of piezoelectric transducers 28. In some examples, transducer portion 32 contains a plurality of piezoelectric transducers 28 for sending and receiving ultrasound signals for echo cardiology imaging, particularly of babies (e.g., baby 38 of FIG. 1). The user positions the transducer portion 32 at a thoracic cavity anterior on the left side of baby 38, so that transducer arrays 28 are positioned nearest to the heart for echo cardiology imaging. Transducer arrays 28 are arranged linearly, running along an array axis. In other words, the linear arrays run from a portion of transducer portion 32 near the lower portion of the thoracic cage, such as the lowest rib, extending along a linear axis to the opposite end of transducer portion 32 nearest to the clavicle of baby 38.

In some examples, the array of piezoelectric transducers 28 may include ultrasound phased array transducers each comprising an array of transducer elements arranged linearly along an array axis, and each said phased array transducers having a field view of about 90 degrees. Initially, the ultrasound beam in columnar, but it gradually becomes divergent, and this divergence result in deterioration of the image quality. The length of the focused beam is directly related to the diameter of the transducer and the ultrasound beam frequency. The field view, however, may increase or decrease depending on the type of piezoelectric crystals that are used, and the field view may increase up to 120 degrees or be lower at 45 degrees, depending on the capability of the crystal. In some examples, the type of signaling of piezoelectric transducer arrays 28 may vary, for example, the individual crystals of transducer arrays 28 of FIG. 1 may receive multiple signals for subaperture signal processing allowing more data to be acquired for imaging and processing the data without losing due to the higher rate of data obtained. Other known signal processing techniques may be used for data acquisition by the transducer array 28.

The crystals of transducer arrays 28 use known techniques for operation. The crystals send and receive the signals. The return reflected signal, or echo signal, provides information for ultrasound imaging. The different crystals each send and receive signals, and based on algorithms and image creation techniques, determine the ultrasound image of the heart, or other organ of the body. The return signal is sent from the crystals of transducer arrays 28 via connector 30 to computing device 2 for signal processing and image determination. Computing device 2 may receive the sent signal from transducer portion 32 and may determine, using algorithms and known cardiac imaging techniques, an image associated with the received signals. Computing device 2 may determine a graphical element representing the return signals, such as graphical element display 20 of the cardiac image.

In some examples, computing device 2 may display the graphical element at a graphical user interface, such as GUI 15. Computing device 2 may further use the received signals from transducer arrays 28 for determining if an abnormality is present in the heart of baby 38 and may also determine if there is a cardiac condition based on the received signals, and determinations from calculations/algorithms that use the received signals from transducer portion 32.

The position of the elements in one group with respect to one another may be known. For example, computing device 2 may have the location of each transducer of transducer arrays 28, and the location of each transducer on transducer portion 32. Computing device 2 may determine the position of one group of transducers with respect to another stiff board containing a second group of transducers. In this example, computing device 2 may need to determine each array's position with respect to another array, instead of calculating each transducer crystal's position with respect to the other transducer crystals. In other words, this configuration also may allow computing device 2 to determine just a slice, or a strip of rectilinear array of transducers, so computing device 2 determines angle from determined positions. Reducing the number of parameters to determine element location may simplify processing of computing device 2 to determine a graphical element display of an image.

The crystals may also acquire data for Doppler imaging. Array crystals may use a Pulse Repetition Frequency to excite the crystals for Doppler data acquisition. The sequence of excitation may differ from the ultrasound image data acquisition to capture the flow volume, etc. of Doppler data acquisition. For example, color flow Doppler may use imaging pulse rate, which is longer than the standard imaging pulse, and may be incorporated in the imaging sequence. Additionally, ultrasound image data acquisition may be line by line with sending the pulse in one direction. Following a standard motion, data acquisition may be with the whole frame of 15 frames per second or higher, such as at around 30 frames per second. In some examples, this rate would not work for long distances and certain data acquisition, such as Doppler, so the Pulse Repetition Frequency needs to be increased to a level fast enough to avoid ambiguity. The frame rate may be, for example, a much higher frame rate, such as 2-3 times the frame rate of the other crystals (e.g., 60 frames/second). The sequence of acquisition of the A lines may change, but fundamentally are not different.

In another example, there may be different ways of exciting the transducer, such as switching between different modes. Depending on which modes are in use, the excitation of the Doppler and the Pulse Repetition Frequency is different. Pulse Repetition Frequency may occur in a first signal mode at the higher rates, and the ultrasound imaging without Doppler may occur in a second signal mode. The user of the device may be able to manually switch between the first and second signal modes, or the computing device may automatically switch in the sequence of data acquisition. The processing for image acquisition may be done in a computing device, or in the transducer device, such as the transducer head, in a small device. The processing may be accomplished on board, such as within the transducer portion 32. In other examples, the processing and signal control may be in a computing device in communication with the transducer portion 32, and may associate with a remote network where data is sent to a remote server, such as a cloud.

The transducer portion may include other elements that may help determine the location of each of the transducer arrays 28, and in some examples, each of the crystals of each of the transducer arrays, of FIG. 1, because the crystals are at different locations on the concave inner side of the transducer portion. In one example, optical fibers may independently give position information about the location of the concave inner surface of the semi-rigid material. Computing device 2 may use plane location information and further determine each transducer location of each plane, such as of the optical fiber at known locations across the concave inner side, in determining an image by computing device 2. In the example of optical fibers, optical elements may use light that does not pass through tissue, bone or tumors, in determining an image. Using optical element may also improve the image because computing device 2 may use the time of the optical signal to determine an image, and may not be as sensitive to different frequencies.

In another example, transducer portion 32 may also include sensors that identify the location or change in relative position of each of the transducer elements with respect to the other. Sensors are not shown in FIG. 1. The sensors may also sense the change in position between the transducer arrays 28 with respect to one another. In some examples, transducer portion 32 may include a plurality of sensors that are evenly spaced across the concave inner surface, and computing device 2 may use the known spacing of the sensors to determine movement. Each sensor element may send sensor data via connector unit 30 to computing device 2 for further determination of a graphical element cardiac image. The image may use the sensor signal data to determine a change in location relative to one another, and from the location of each sensor element, the position or movement of transducer arrays 28, and in some example the position of the crystals of each array, determined by any bending, flexing, movement of each of transducer arrays 28 being mounted on semi-rigid material.

In yet other examples, transducer array 26 may include transducers that operate at different frequencies. Each transducer may have a unique frequency. The frequency may identify the transducer and the location. Different frequencies may create a pattern of waves to determine the configuration of an array, and ultimately, image of the heart. One challenge in using transducer arrays on newborns in that the newborn's chest cavity is small. For example, newborns will have reflections of the waves if tissue is too close, swamping the signal. More space, or a longer travel path, allows for a longer and dearer signal. In one example, the system may operate transducers at higher frequencies and computing device 2 may process the signal with a higher frequency for the correct image resolution. For example, with the transducers send a pulse at a frequency for newborn 74, the signal may scatter off tissue and get reflectives. Computing device 2 may automatically set the frequency based on factors for a newborn 0 to 14 lbs., or the user may select the frequency. Computing device 2 may use the arrival time and strength of reflectives received by a signal receiver to determine the image created by echo module 10. Image 20 may be, for example, a depiction of the received signals to illustrate an image type of tissue (e.g. bone, muscle, organ, etc.). Due to the newborn size, the time difference of arrivals may be too short to determine the tissue type. Additionally, some of the structures, such as bone and cartilage, in newborns may have a different bone density as an adult, and thus, echo module 10 may have to calculate the signal to determine image 20 to compensate for the time difference of arrival and density.

The transducer portion 32 may have a concave inner side. The curve shape may be consistent along the arch, or the cure may vary in degrees. For example, the arch with a consistent curve when transducer portion 32 only covers the baby's anterior thoracic cavity on the left side, but in other examples, transducer portion 32 may be wider, so transducer portion 32 extends around the left anterior axillary line (or side) 36 of the baby under the left arm, and transducer portion 32 curves to fit closely to the body, curving at an angle around the left anterior axillary line 36 that is greater than the angle of curve or arch (if there is any for this portion of the transducer portion 32) over the front or anterior portion near the heart and left pectoral muscle. The concave inner side may allow transducer portion 32 to lie in more uniform contact with the exterior left side of the thoracic cavity on the anterior side of baby 38.

Transducer arrays 28 may be mounted or secured directly to the concave inner side or secured to a layer that is mounted or secured to the concave inner side of the transducer portion 32. For example, the concave inner side of transducer portion 32 may secure to a layer of mesh material mounted upon the concave inner side. Securing techniques may be gluing, sewing, molding, mounting, or other techniques that secure the transducer crystals to the mesh material. The concave inner side is rigid so that the transducer crystals do not move. In some examples, the concave inner side may bend slightly, being semi-rigid, so that the transducer portion 32 may be held against the skin of baby 38. The fully rigid or semi-rigid transducer portion 32 may include certain materials, such as at least one of: polyethylene, polypropylene, vinyl, polyamides, polyesters, polyurethanes, polystyrene, copolymers, rubber, silicone, latex and thermosets. The composition make up of each of these compounds determines the rigidity and flexibility of the material. In some examples of the invention, transducer arrays 28 may be on a stiff surface. A stiffer surface allows echo module 10 to determine image 20, because the transducer crystals that make up the arrays have limited movement and maintain spacing relative to one another. Echo module 10 may determine the location of each of the crystals, and based on the location and the reflectives, determine the location of the tissue, i.e. the heart, relative to each of the transducers. Additionally, mounting transducer crystals to a rigid surface or semi-rigid surface may improve image quality, as the limited movement of the crystals may improve forming a beam, because the rigid surface determining the time difference of arrivals uses the known position and orientation of the array members, i.e. the transducers.

In addition, the rigid or semi-rigid transducer portion 32 may also include polymeric or polymer-coated particles fused into a macroscopically semi-rigid structure to provide high acoustic attenuation. Such materials may make transducer portion 32 rigid enough so that the transducer arrays 28 do not move position and have the same relative position on the rigid surface. In examples when the transducer portion 32 is semi-rigid and may slightly bend, transducer portion 32 may further include location elements for determining the position or angle of the elements from one another in transducer arrays 28. The semi-rigid material may slightly bend, so that if wrapped against the left thoracic cavity, the transducer portion 32 will conform to the shape of the chest wall. The material is semi-rigid as it bends slightly, but with constant force pushing so that when the material releases, it springs back into the substantially the original shape. In echo cardio imaging, little air may be present or the image quality will be poor or unreadable. Thus, contouring to the body of baby 38 may reduce the air in between the transducer arrays 28 and the outer chest wall of the left thoracic cavity anterior side of baby 38. The concave inner side shape allows a closer fit to the left chest wall of the thorax of baby 38. The curved shape may have an even curve to it or it may be more curved near one side, so that the transducer portion 32 fits the curve of the left rib cage, particularly around the anterior axillary line, of the baby. Thus, the material must be substantially rigid, enough to hold the piezoelectric transducer arrays 28 in place, but semi-rigid to allow minimal flexibility so the form conforms to the anterior axillary side of baby 38.

In one example, ultrasound imaging gel would be used to remove any air pockets between the skin and the transducer crystals. Other known techniques, such as gels or other compounds, that are known to those in ultrasound imaging may also be used to remove air to improve image quality. A layer of gel or other ultrasound compatible fluid (not pictured in FIG. 1) may fill a pocket forming a layer on the concave inner side, so that the fluid conforms to the curves of baby 38 so that air may not fill any gaps.

In one example, the transducer portion 32 may also include an additional heatshield layer attached to the inner side of the transducer portion 32. The heatshield layer may be between the newborn's skin and the inner concave side of transducer portion 32. The layer may be an existing layer of fluid or echocardiography compatible gel, or in other examples, it may include a layer, such as polymer material, sealed to the transducer portion 32 with a small capped opening, which allows additional echo compatible fluid, such as saline or a gel, into the area and replacing air in the area. This pouch or fillable layer acts as the heatshield, or allows heat transfer so any heated crystals dissipate the heat to a degree prior to reaching the newborn's skin. This layer would allow the echo waves to travel without air and the layer may act as a heatshield when the crystals become heat, so that the newborn is not burned or injured during image acquisition. Gel may also be added to the outside of the heatshield layer, between the layer and the newborn's skin, removing air that could reduce image quality.

In some cases, the user may control the use and frequency of the transducers with a user interface on computing device 2. In some examples, the user may control which users are used and may control the frequency of the transducers. In other examples, computing device 2 may determine and control the transducers of transducer arrays 28. Computing device 2 may activate by sending and receiving signals to certain crystals of the transducer arrays to fit the size of the heart, so that the transducers nearest the target areas of the heart send and receive signals. In some examples, computing device 2 may improve image clarity by changing the frequency of a transducer. In other examples, transducer arrays 28 may include transducers that function at different frequencies. Computing device 2 may select the transducers that operate at a particular frequency. Computing device 2 may change the frequency by sending and receiving signals to transducers operating at a different frequency. Computing device 2 may select all or some of the transducers operating at a particular frequency.

In some examples, transducer portion 32 may have a securing portion 34 extending from transducer portion 32 and holds transducer portion 32 firmly against the chest of baby 38, limiting the motion of the transducer crystals. Securing portion 34 may include flexible material, so that the material may stretch securely around and conform fit around the thorax of baby 38. Securing portion 34 may wrap around the anterior axillary line of baby 38, holding transducer portion 32 in place and limiting the movement, so that when baby 38 moves, transducer portion 32 moves too. In some examples, securing portion 34 extends around the back of baby 38 and is secured on the posterior side or the side of baby 38. Securing means may be Velcro, buttons, sticky material, ties, zippers, snaps, hooks, and any other type of closing means for material. Velcro is a fastener made up of two strips of thin plastic sheet, one covered with tiny loops and the other with tiny flexible hooks, that adhere together when pressed together and separate when pulled apart. In other examples, the securing portion 34 may secure to the side of baby 38, such as at the midaxillary line.

In one example, transducer portion 32 may be next to securing portion 34. Securing portion 34 may secure to transducer portion 32. Securing portion 34 may be an additional layer of multiple layers of transducer portion 32, such as a layer on the opposite side of the transducer portion 32 opposite from concave inner side 38, limiting the motion of transducer portion 32. In other examples, securing portion 34 may not be attached to transducer portion 32, but tightly wrapped around baby 38 with transducer portion 32 next to the skin of baby 38. In another example, securing portion 34 extends from the sides of transducer portion 32 without extending on the opposite side of the concave inner side.

The securing portion 34 attaches to transducer portion 32. For example, the securing portion may be two separate pieces, each extending from a side of transducer portion 32. A first securing portion extends from the left side, or the side nearest to the axillary side 36 of baby 38, and the first securing portion may extend from the right side from the left side nearest to the sternum. A second securing portion of securing portion 34 may extend from the top, or clavicle side, of transducer portion 32. The second portion may extend around the left shoulder of baby 38 and connect to the first portion, pulling transducer portion 32 securely positioning the concave inner side of the semi-rigid structure against the anterior side of the thoracic cavity. The first and second securing portions may securely connect at the posterior side of the thoracic cavity. The first securing portion may connect to the second securing portion securely positioning the concave surface of the semi-rigid structure tightly against the anterior side of the thoracic cavity, further wherein the first and second securing portions securely connect at the posterior side of the thoracic cavity.

All portions of securing portion 34 may include materials that are flexible and in some examples, semi-elastic, and in other examples elastic, such as neoprene, gauze, cotton, polyester, microfiber and rubber. The flexible material may contour to the shape of the thorax and the semi-elastic qualities may allow transducer portion 32 to stay against the anterior side of the thorax, with minimal movement for imaging, extending around different body shape and sizes of the thorax. The semi-elastic material may all hold transducer portion 32 against the chest wall and limit movement from that position. The material may only have semi-elastic qualities, because transducer portion 32 must be held firmly in place, and too much elasticity would allow movement. Additionally, the semi-elasticity mush hold transducer portion 32 firmly against the anterior thoracic cavity for reducing a gap between the transducer portion and the anterior thoracic cavity. Air filling the gaps reduce the quality of the ultrasound imaging, and in some cases, need a gel or other ultrasound compatible material to fill the gaps or air pockets.

In another example, the ultrasound wrap may also include a second securing portion (such as a shoulder securing portion). Wherein the shoulder securing portion extends from the clavicle side of transducer portion 32 and is configured to extend to the posterior side of the patient around the shoulder of baby 38 and over at least a portion of the left clavicle. A first securing portion 34 extends from a first axillary side of the transducer portion such as the line between transducer portion 32 and first securing portion 34. "Transducer portion" is also referred to as the "transducer housing" herein. First securing portion 34 may be configured to extend around baby 38 and attach to transducer housing 32, for example opposite side that first securing portion 34 extends from on the axillary side. In another example, first securing portion 34 may be configured to attach posteriorly to a third securing portion, which extends from transducer portion 32 on the opposite axillary side that first extending portion 34 extends from (see, e.g., FIG. 5 where third extension portion may be element character 150). A second securing portion may extend from a clavicle side of the transducer housing (e.g. second securing portion 190 of FIG. 5). In other examples, securing portion 34 may include an extension that is a separate piece of material, extending from transducer housing 32 to the posterior side of the patient around the shoulder of the patient and over at least a portion of the clavicle. (See, e.g., shoulder portion 190 of FIGS. 1 and 5). In other examples, first extending portion 34 may have a slit in the material for the arm to go through.

In other examples, transducer arrays 28 may be a wrap that extends around the chest of newborn 38. Wraps may improve securing of transducer arrays 28 to the chest cavity limiting movement of the transducers by extending around the thorax. A wrap configuration also allows transducer placement on the opposite side, or the wrap portion in contact with the dorsal side of the thorax of newborn 38. Placement of transducers on both the ventral and dorsal side of the thorax may allow receiving signals on the ventral side and also dorsal transducers may receive signals that travel through the thorax to be received. These signals may assist computing device 2 to determine the location and tissue type. In addition to receiving additional signal on the dorsal side of newborn 38, the wrap may extend the wave travel path, contributing to a clearer image.

In the wrap configuration, transducers may be placed on the wrap all around the thorax, allowing imaging through the thorax using techniques used to image the structure and core of the Earth. Additionally, earthquake seismograph techniques may determine the time difference of arrivals when transducers are used on the dorsal side. In some examples, the user may control the transducers around the wrap to solve the angle of the transducers with respect to one another and may pattern and control the signal to determine an image through the thorax, instead of a reflection of the signal. For the purposes of illustration, FIG. 1 only shows transducer crystals on the transducer portion 32.

Transducer portion 28 may have a connector unit 30 that connect to and communicates with computing device 2. In other examples, connector unit 30 may be computing device 2. Computing device 2 may communicate transducer arrays 28 for imaging. For example, transducer arrays 28 may receive signals from computing device 2, and in some examples, may send data to computing device 2 for imaging and further abnormality detection.

UI device 4 of computing device 2 may function as an input device for computing device 2 and as an output device. For instance, UI device 4 may function as an input device using a resistive touchscreen, a surface acoustic wave touchscreen, a capacitive touchscreen, a projective capacitance touchscreen, a pressure sensitive screen, an acoustic pulse recognition touchscreen, or another presence-sensitive screen technology. UI device 4 may function as an output device using any one or more of a liquid crystal display (LCD), dot matrix display, light emitting diode (LED)

display, organic light-emitting diode (OLED) display, e-ink, or similar monochrome or color display capable of outputting visible information to the user of computing device 2. UI device 4 of computing device 2 may include a presence-sensitive screen that may receive tactile user input from a user of computing device 2. UI device 4 may receive the tactile user input by detecting one or more taps and/or gestures from a user of computing device 2 (e.g., the user touching or pointing to one or more locations of UI device 4 with a finger or a stylus pen). The presence-sensitive screen of UI device 4 may present output to a user. UI device 4 may present the output as a user interface (e.g., graphical user interface (GUI) 15), which may be related to functionality provided by computing device 2. For example, UI device 4 may present various functions and applications executing on computing device 2 such providing a graphical display of echo image 20 as a result of the signal received from transducer portion 32, controls for controlling transducer portion 32, etc.

Computing device 2 may include user interface ("UI") module 6, signal module 8 and echo module 10. Modules 6, 8 and 10 may perform operations described herein using software, hardware, or a mixture of both hardware and software residing in and executing on computing device 2. Computing device 2 may execute modules 6, 8 and with multiple processors. Computing device 2 may execute modules 6, 8 and 10 as a virtual machine executing on underlying hardware.

UI module 6 may perform one or more functions to receive data, such as user input or network data, from components associated with computing device 2, such as echo module 10, and send such input to other components associated with computing device 2, such as echo module 10. Using the data, UI module 3 may cause other components associated with computing device 2, such as UI device 4 provide output based on the data. For instance, UI module 3 may receive data from echo module 10 that causes UI device 4 to display the image of a heart at the graphical user interface display at GUI 15. UI module 6 may be implemented in various ways. For example, UI module 6 may be a downloadable or pre-installed application or "app." In another example, UI module 6 may be implemented as part of a hardware unit of computing device 2. In another example, UI module 6 may be implemented as part of an operating system (e.g., operating system 60) of computing device 2. In general, computing device 2 may execute applications stored on the device or may execute applications and programs from a network. For example, echo module 10 may be an application that is preinstalled on the device or computing device 2 may download the application of echo module 10 for controlling the transducer array 28, interaction with a user, and sending data to an imaging network for further analysis and data acquisition.

Echo module 10 may include functionality to perform any variety of operations on computing device 2. Echo module 10 may be an application that includes a text application, photo viewer, video application, medical records application, email application, VPN network application, image capture application, audio application, word processor, spreadsheet, web browser, multimedia player, server application, etc. As described with respect the example of FIG. 1, echo module 10 may include functionality of an imaging and condition recognition application that the user (not shown in FIG. 1) to image the heart. Echo module 10 may be implemented in various ways on computing device 2. For example, echo module 10 may be a downloadable or pre-installed application or "app." In another example, echo module 10 may be part of a hardware unit of computing device 2.

The term "image data" as used herein is a broad term encompassing as its plain and ordinary meaning including, but not limited to: signals, sound waves, data files, photos, images, audio, video recordings, graphics, user input during imaging (or associated with an image file), sensor crystal data, and combinations thereof. Image data may also be the determined heart rate, heart function, blood pressure, etc. calculated from the signals received from transducer arrays 28. Known techniques and algorithms may be used for calculating and determining such cardiac data and determining the resulting image of the heart. Image data may be used in algorithms associated with cardiology and cardiac function and adapts to any data that a computing device is capable of capturing, receiving or storing. While this disclosure uses the non-limiting example of an ultrasound image or as echo image data to illustrate various techniques of this disclosure, the techniques of this disclosure may be applied to other types of objects and are not limited to echo cardiology images. As shown in FIG. 1, GUI 15 may include a user interface that allows a user, such as a nurse, imaging tech, doctor, or ordinary unskilled person who uses transducer portion 32, to interact with computing device 2. GUI 15 may include graphical content, text, images, videos, audio, or any other visually displayable graphical object or audio object. User 2 may interact with GUI 15 to control transducer portion 28, view images 20, send data to an associated medical data network 24, determine an abnormality 22 (i.e., an abnormal cardiac condition), etc.

In one example, the user may enable transducer arrays 28 to begin scanning by user input at a graphical control displayed within GUI 15. Once the user, such as positions transducer portion 32 on the correct left anterior portion of the thorax, transducer arrays 28 may begin to sense cardiac function and an indication may appear as a graphical output on GUI 15 indicating correct placement. The user may secure securing portion 34 by pulling the semi-elastic material around the back of baby 38 so that there is no slack in the material of securing portion 34 and the transducer portion 32 is securely held against the anterior chest wall. The best signal location of transducer portion 32 may be at between the left clavicle and the lower (tenth) left rib at an anterior side of the thoracic cavity. Transducer arrays 28 may span the concave inner side of transducer portion 32, so that piezoelectric crystals are spread, in some examples evenly, across the concave side to cover between the left clavicle and the lowest rib. Baby 38 may be a newborn, or small in size, so that transducer arrays 28 may be 6 to 8 inches in length and 6 to 8 inches wide. The semi-rigid material must span at least 6 to 8 inches as well, or where the transducer crystals are located, so that the crystals have limited motion. The crystals must be stationary or have little movement for improved image quality. Securing portion 34 may be tight enough around baby 38, so that there is little to no air between the concave inner side of transducer portion 32 and the anterior chest tissue of baby 38, but not too tight so that breathing is compromised or the lungs have difficulty expanding. Securing portion 34 may then fastened together the ends of the wrap, for example, when the first side may secure with Velcro, on the posterior side of baby 38 or at the right or left side of baby 38. Velcro is a fastener made up of two strips of thin plastic sheet, one covered with tiny loops and the other with tiny flexible hooks, that adhere together when pressed together and separate when pulled apart.

In one example, echo module 10 may have a plurality of condition identifiers stored in computing device 2 that may indicate a cardiac abnormality or condition. Echo module may determine a respective weighted probability for the received image data (and associated data) by comparing the received image data to each of the condition identifiers. The weighted probability may, in one example, correspond to a likelihood that baby 38 has a cardiac abnormality. An echocardiogram uses ultrasound to evaluate heart muscle and heart valves. Thus, echo module 10 may detect or identify heart disease or heart valve disease. Features that may determine heart or heart valve disease may include thickening and function of the heart valve. Some examples of cardiac abnormalities that may be indicators are the size of your heart, the thickness of the ventricles, heart structure, valve structure, and flow through the heart and valves. A large heart may indicate high blood pressure, leaky heart valves, or heart failure. Increased thickness of the ventricles (the hearts lower chambers) that may indicate high blood pressure, heart valve disease, or congenital heart defects. The size, structure, and movement of various parts of your heart are all viewable through echocardiography. Specific heart areas may include the heart valves, the septum (the wall separating the right and left heart chambers), and the walls of the heart chambers. Also viewable using Doppler ultrasound shows the movement of blood through your heart. Doppler sound data, video, or image data may also be considered image data for heart condition/abnormality detection. Echo scan of your heart scan may provide accurate pictures of the heart muscle, the heart chambers, and structures within the heart such as the valves that may allow indicators of a heart condition to be viewable. Echo module 10 may automatically use the echo scan to automatically determine any abnormalities or indications of heart conditions.

In another example, computing device 2 may determine an abnormality based on the return echo signals from transducer array 32, and may also provide the graphical element and based on the image data, by applying weighted probability techniques and algorithms. Echo module 10 may determine a weighted probability that represents the likelihood that baby 38 has a cardiac condition and if the condition associates with an abnormality. Computing device 2 may base the weighted probability for the cardiac condition on image data and any associated data and determine a probability for each of the indicators received. For example, the image data may include indicators, such as thickness of the heart ventricles, valve thickness, or structural abnormalities that indicate a heart defect. In other examples, indicators may also include, blood pressure and blood flow into, through and out of the heart may indicate a heart defect or heart failure. Computing device 2 may look at the image data for all the indicators to determine a weighted probability for the physical characteristics of the heart, blood flow, etc. for each and determine the likelihood of a condition. In other examples, computing device 2 may further determine a weighted probability that the weighted indicators are associated with a specific cardiac condition of the plurality of conditions stored in computing device 2. In some examples, computing device 2 may determine that the weighted probability may determine a low likelihood of a serious cardiac condition and in other examples, the cardiac condition may determine a high probability that the highly weighted structural features (indicators) and the flow (indicators) have a greater likelihood of association with (or indication of) a structural heart defect. Computing device 2 may highly weight the probabilities when determining that the indicators are associated with a heart condition and an abnormality, and further more heavily weight those structural and functional cardiac conditions, and in some cases, more heavily for structural and functional abnormalities, particularly those that need immediate medical attention. For illustrative purposes only, this example focuses on structural heart defects, but is not limited to this and computing device 2 may use other heart indicators that are known in the cardiac medical arts may be used to determine a heart condition or abnormality.

In addition to the heart structure anatomical indicators, in some examples, the geographic location of racial information may also indicate certain cardiac conditions or abnormalities. Other data may be the child's birth date, weight, height, and other physical data about the child that a user may input into computing device 2 or by scanning a medical data chip, receive a data file, etc. Racial and geographic information is important to determine if higher rates of certain conditions or genetic features are present. Computing device 2 may also use medical history or population based medical data to determine a weighted probability for a condition. In some areas, not only genetic factors but viral infections may lead to cardiac conditions. Computing device 2 may include this data in the weighted probability determination of a possible condition or abnormality. In generating the weighted probability, echo module 10 may be configured to more heavily weight certain factors, such as structural abnormalities, medical history of baby or family, and a thickening of certain structures, etc. Heart conditions may include abnormalities, but may include other indicators as well. In one none limiting example to show this difference, in heart failure, a heart condition, the heart weakens and is not able to pump as well over time. During heart failure, the pumping level may still be with a normal range, indicating no abnormality, but the reduced pumping volume may indicate the heart condition of heart failure. Computing device 2 may store indicators, including abnormalities, and associate them with a specific medical condition or term(s), and store the association with the image and associated data to be used for further treatment or diagnosis.

Echo module 10 applies weighting factors to each piece of information included in the weighted probability calculation and generates a weighted probability for each of the available stored conditions and abnormalities. Responsive to determining the weighted probability for each of the heart conditions and abnormalities, echo module 10 may refrain from selecting or determining a heart condition having a respective weighted probability value greater than a threshold value. In some examples, computing device 2 may determine a graphical element display based on the weighted probability displayed within GUI 15. In one example, higher weighted probabilities above a pre-determined threshold value may cause echo module 10 to output at GUI 15 a graphical element that indicates an abnormality 22. In another example, below the predetermined threshold may cause computing device 2 to output at GUI 15 an indication to rescan or an indication of a normal scan or completion of scanning. In examples where computing device 2 may determine multiple conditions, the threshold value may be dynamically determined based on the calculated weighted probability values such that only the top three, five, or some other configurable number of conditions that have weighted probability values that meet or exceed the threshold value.

In one example, determining the filtered content is based on a threshold that may be based on a predetermined value. Echo module 10 may set the value or other modules of computing device 2 configured to do may set the value. The value may be a specific numerical value based on the weighted probability. The threshold may be based on a percentage of the weighted probability. Alternatively, the threshold may be a specific number of the "top" weighted probability values, for example, so the top three weighted probability values are selected. In another example, selecting the object may be based on weighted probability by comparing a degree of similarity between the condition identifiers the image data and one or more characteristics associated with the respective condition or abnormality. When the weighted probability is greater than the threshold, computing device 2 may select the respective object for filtering, refraining from including the object in the output at the graphical user interface. When the weighted probability is not greater than the predetermined value, Computing device 2 may select the respective object for output at the graphical user interface, GUI 15.

In one example, outputting, by computing device 2 and at GUI 15 of computing device 2, the graphical element. Echo module 10 provides the condition and abnormality determination of selected image data sent by transducer arrays 28 via connector unit 30 to UI module 6, and then UI module 6 outputs an updated user interface (e.g., GUI 15) for display at UI device 4. Echo module 10 receives image data and determined heart condition and abnormality data and stores information about the determination for later retrieval and inclusion in determining weighted probabilities for the next time content is filtered, and a probability score is generated by echo module 10. Because a physician or trained imaging specialist may also use the device and system, Echo module 10 may also output an indication for the user, the nurse, physician or technician, to input further data or control imaging of transducer arrays 28 either at the tie of imaging or after imaging concludes. The input data may also be weighted and part of the condition diagnosis and stored in computing device 2.

In some examples, transducer arrays 28 may scan in different modes, for example, a first mode may be automated, so that little user input is require, except position transducer arrays 28 and tightly secured securing portion 34 around baby 38, and transducer arrays 28 will repeat scanning when a signal to repeat scanning is received (e.g., computing device 2 determines that the image quality is poor and a new scan commences for a better quality). In a less automated mode, second mode for example, the user may control scanning and imaging with more input, such as controlling each array of transducer arrays 28. The user may switch modes during use, for example, if a physician uses the transducer wrap 26 and notices that the images acquired are of poor quality and difficult to read or see features of the heart, then the physician may switch to the second mode and control transducer arrays 28 to acquire an image with better quality. Echo module 10 may also have a second mode, parental/corporate control, where content cannot be viewed. In the second mode, a passcode or access code may be entered to access the user account so that the user can input data and control transducer arrays 32 (e.g., FIG. 3 for example of the second mode).

Computing device 2 may save the image data. Storing the data may be local, such as in echo module 2 associated with the graphical element, or in a remote server, such as a medical communication network or in the network of the respective application. Stored objects may be used for later determinations of weighting probabilities for filtering content of applications. Any input data may also be stored and used for updating weighted probabilities for future use. In other examples, filtered objects are not stored on any device or network. An associated medical network may also provide echo module 10 with data for updating weighted probabilities and indicators of conditions.

Techniques of this disclosure may provide one or more advantages. For example, by automatically identifying heart condition indicators and suggesting/identifying possible heart conditions associated with the indicators, techniques of this disclosure may reduce the amount of time required to read an echo and diagnose heart conditions. Techniques of this disclosure may improve indicator identification and condition determination by "learning" conditions associated with indicators over time, e.g., by analyzing the context of the indicators associated with conditions and previous conditions selections. By reducing the need for finding indicators in an image initially presented to a user during image acquisition and by intelligently selecting a potential heart condition to suggest to the user, techniques of this disclosure may provide a better user experience and may reduce the time and effort required by the user to read an echo image.

The disclosure includes many examples for application to a newborn or pediatrics. However, the medical device and system of this disclosure may apply to adult as well as newborns, and any size or age of a person receiving an echocardiogram.

FIG. 2 is a block diagram illustrating an example of a computing device for use in echo cardio imaging, in accordance with one or more aspects of the present disclosure. Computing device 2 may contain a storage device 30 may include a volatile or non-volatile computer readable storage medium that is able to store such as software programs and data to implement the functionality of the lane determination system. In some examples, storage device(s) 48 may include non-volatile storage elements, such as magnetic hard discs, optical discs, floppy discs, flash memories, or forms of electrically programmable memories (EPROM) or electrically erasable and programmable (EEPROM) memories. For example, storage device(s) 48 may include Random Access Memory (RAM), Read Only Memory (ROM), flash memory or any other form of long term or short term memory, although without limitation thereto. In some embodiments, the memory may also include hard disk drive, floppy disk drive, tape drive, secure digital (SD) card, digital versatile disc random access memories (DVD-RAM), or any other appropriate form of computer readable storage medium. Processor(s) 6 is operably connected to a communication unit(s) 44, an input device(s) 42, an output device(s) 46, a user interface (UI) device 4 that includes a presence-sensitive screen 72, storage device(s) 48 and communications channel(s) 50. Processor(s) 40 may also be connected to other modules/devices (not shown) within Computing device 2 or connected externally via an appropriate interface. Processor(s) may include, but not limited to, microprocessor unit, graphical processor unit, digital signal processor or any other appropriate processors that have the capability to execute computer program instructions on data to produce the expected output. A processor(s), not shown in FIG. 2, may include a plurality of components from a list including registers, buffers, control logic, data lines, arithmetic logic unit (ALU), floating-point unit (FPU), and other appropriate components for performing operations including arithmetic, logical, control, input, and output specified by the instructions in a computer program.

Computing device 2 may also include hardware and/or software modules including antenna to communicate wirelessly to the Internet, a camera device to capture photo and video, a microphone to receive image data from transducer array 32, capture audio, a call module, short message service (SMS) module, a media player module to play multimedia content (for example: music and movie), and an Internet web browser (for example: Firefox and Google Chrome), and medical data module for viewing medical files and adding echo scan data. Computing device 2 may also have additional applications installed such as VPN network access, medical records, echo scan imaging and analysis, calculator, calendar, text editor, and other appropriate application programs.

In some examples, storage device(s) 48 may include an image module 56, which may execute machine instructions or computer instruction to produce an output on output device 46 or send data to a peripheral device interface or other appropriate interfaces, and may use one or more of processor(s), which may be one or more from a list including single processor, multi processors, single-core, and multi-core processors. Image module 56 may cause processor(s) to execute machine instructions or computer instructions to produce an output on output device(s) 46 or send data to a peripheral device interface or other appropriate interfaces. In alternative forms of a user device, a plurality of hardware processors, types of memory, and data busses (not shown) may be present. Identification module 62 may include indicator module 66 and condition module 68. Image module 56 may send determined output graphical display data to UI module 52 for displaying the determined content at presence-sensitive screen 72. In some examples, presence-sensitive screen 72 is output device 46.

In another embodiment, user input (UI) module 52 may receive user input through one or more of input device(s) 42, such as touch screen, audio, visual, keyboard, and other haptic based devices. The scan module 58 may execute instructions that include program instructions stored in memory within the storage device(s) 48 (e.g., image 70, condition 72, and echo data 74), stored externally, or transmitted by means of radio waves or electromagnetic waves. Identification module 62 may retrieve device data from storage device(s) 48, which is a data store for computing device 2.

After the user positions the transducer arrays (not shown in FIG. 2, but shown in FIG. 1) on the newborn baby and secures the wrap around the baby, scan module 58 may receive user input at user interface device 4, indicating enabling the echo application and, in some examples, enabling password protection for accessing the echo imaging application or patient files. When a user enables scan module 58 on computing device 2, scan module 58 sends a signal out either wirelessly or through hardware to communication unit 44. Communication unit 44 may send and receive data from communication unit(s) 44 via communications channel(s) 50, sending and receiving data to the intended application or device associated with transducer array(s) 32 (e.g., shown in FIG. 1). For example, connector unit 30 may receive and further communicate the signals to transducer array 32. Scan module 58 may control the transducer arrays, such as sending and receiving signals from the respective crystals of a signal array or of multiple arrays simultaneously. In some examples, the signal strength may be controlled. Transducer array(s) 28 fro FIG. 1 may send signal data via connector unit back to scan module 58. In the example when scan module 58 first receives the data, scan module 58 may send the received signal data to image module 56. Image module 56 may determine an image of the heart based on the received data from transducer arrays. Image module 56 may determine the image based on other data such as position sensor data, identifying the position of the crystals and any movement of the crystals during imaging. The data is then sent to computing device 2, for example to image module 56 or scan module 58. Image module 56 may then send the determined image data, and any associated data received from transducer arrays 32, to identification module 62. Identification module 62 may receiving the data directly from scan module 58 in some examples or from image module 56. Communication unit(s) 44 may receive data about the image or other condition identification related information (e.g., geographical data, family medical data, genetic data, population data, etc.) from a remote server via the wireless network or other appropriate communication network, such as communicating through one or more communication technologies including cdma2000, WCDMA, WiMAX, Wi-Fi, 25 Wi-Fi Direct, BLUETOOTH, GPRS, 3G, 4G, LTE, satellite based communication, and other appropriate communication technologies that will be known to an ordinary person skilled in the relevant art. (e.g., Wi-Fi, a peer-to-peer connection such as BLUETOOTH or Wi-Fi Direct, or other appropriate form of connection).

Further, identification module 62 may automatically determine a possible cardiac condition or abnormality. Identification module 62 may cause processors to connect to appropriate storage device 48 through identification module 62 to retrieve and store data. In other examples, computing device 2 may be connected to external devices through wired or wireless connection as appropriate, or through Universal Serial Bus (USB) or other wired connections. For example, identification module 62 may include mechanisms to receive data or send data to a remote server, such as a medical records or medical emergency alert system, using known techniques.

Identification module 62 may send the data to indicator module 66 to determine condition identifiers. In one example, condition identifiers may include cardiac data about anatomy and function, signal information, location information, imaging date, user settings, position, temperature, heart rate, pressure, and any other data about a specific condition or cardiac abnormality. Indicator module 66 may receive the image data and any other associated data associated with baby 38 e.g., family medical history, population data, etc.) during the echo scan and indicator module 66 may determine any indicators in the received data. Image data may associate with the graphical image of the echo, and other associated data may associate with the non-graphical data of the echo scan. In some examples, indicator module 66 may determine a weighted probability for each of the determined indicators of the received data, for the likelihood that the received data is an indication of a condition, for example, indicator module 66 may determine whether a probability exists for each determined indicator. If a probability does not exist between a suggested sharing service and the indicator, indicator module 66 may generate a corresponding matching score, or probability. In some examples, a probability may be a value in a range between 0-1. In some examples, a probability may be initialized to a value of 0.5. Once identification module 62 locates user preferences, indicator module 66 may compare the determined data with the characteristics of the conditions indicators. Based on the comparisons, indicator module 66 may determine the probability based on a comparison of probabilities determined for previously identified indicators, stored in a data storage (e.g., condition 72 or echo data 74). The indicators and the associated weighted probabilities may then be sent to condition module 68. In some examples, only certain values or scores may be sent to condition module 68. For example, applying a threshold value to determine which indicators to select and send to condition module 68 for further condition analysis.

Condition module 68 may determine a present condition, from the available conditions in computing device 2, and may determine which conditions is most likely associated with certain indicators individually or in combination. For example, specific conditions may be frequently selected by condition module 68 or by input from the user, may be recently used, may have characteristics of a condition, or may be relevant to a context of imaging, including information about newborn baby 38 (e.g., age, size, weight, oxygen saturation levels, pulse rate, etc.). Condition module 68 may receive the indicators, weighted probabilities, values, image data, and any other associated data, from indicator module 66. In some examples, condition module 68 may also receive probabilities for previously identified indicators, determined condition(s) associated with the indicators, and in some examples the determination of no existing condition, which may be in a data storage, such as condition 72. Once the data is received from indicator module 66, condition module 68 may compare the indicators with conditions to determine if baby 38 likely has an indication of a cardiac condition. By comparing the indicators with the conditions, condition module 68 may match the indicators to an associated condition. Condition module 68 may order the indications based on the resulting probability value to a threshold value, initially determined by indicator module 66, to determine which indicators to select to determine a condition. By setting a threshold value, identification module 62 may filter the indicators to improve the accuracy of the identified condition identification. For each indicator with a probability value that is lower than the threshold value.

In some examples, the indicator weighting may have a ranking to them, and other examples a threshold may determine which conditions are likely present in baby 38. Weighted probabilities indicate a probability that the indicator may likely associate with a cardiac condition that may need medical treatment. Indicator module 66 may more heavily weight certain factors, such as ventricular thicknesses greater than the average thickness for a baby of the same age, weight and height, or if the mother has a potentially fatal heart condition with thick ventricles as an indicator. Additionally, user input data may also be weighted more heavily, such as if the user inputs other associated data, such as turning blue, low blood pressure, passing out, etc., that the user enters at presence-sensitive screen (GUI) 15, more than, for example, metadata associated with the date of scanning the patient. In some examples, scan module 58 may have certain user preferences, such as selected settings, or scanning modes that may also weight certain indication criteria differently, such as a standard mode (i.e., automated) or a coarse (i.e., skilled user may input) mode. The settings may also look for certain characteristics of the scanned data and specific indicators to further look at a certain condition or abnormality.

Indicator module 66 may update the weighted probability based on user input, or user indication to include it in the filter. For example, when the user indicates including an object in the graphical display by inputting data into computing device 2. Indicator module 66 may select one or more of the indicators available on computing device 2 as indicators of heart conditions in newborns. Indicators of heart conditions may include indicator module 66 determines that a trained professional would likely identify as an indicator. In some examples, indicator module 66 includes information about the location of transducer array 32 to determine abnormalities of that location or angle during imaging. Condition module 68 may select possible heart conditions based on the weighted probability of an indicator, or a plurality of indicators, being associated with a particular condition and the likelihood of a possible identification (or indication) with a condition or abnormality. The weighted probability may, in one example, correspond to a likelihood that each indicator, or the plurality of indicators, indicate a particular heart condition. Condition module 68 may determine a weighted probability that indicates a probability that one or more indicators are in association with a heart condition for newborn baby 38. Computing device 2 may base the weighted probability for each heart condition on information about the heart condition, characteristics of each indicator, characteristics of each condition, a context of computing device 2, and a context of the object being imaged. In generating the weighted probability, condition module 68 may be configured to more heavily weight certain factors, such as prior association, user selections, than other factors, such as weight and health of newborn.

Condition module 68 may send the determined cardiac conditions to user UI device 4 for display as a graphical element. Computing device 2 may output a graphical element that indicates the determined condition(s) at presence-sensitive screen 72. Image module 56 may also send image data to user interface device 4 for displaying the graphical element of the heart at presence-sensitive screen 72. Image module 56 may determine the graphical element for displaying on output device 46 based on element creation calculations that may use location data of the location of each of the respective crystal elements of transducer arrays 28, and in some cases, data from a location sensor element also received from transducer portion 32.

The user may input an indication associated with sending the image to a computer network for further analysis by trained medical professionals. In other examples, the user may rescan newborn baby 38 for additional images. In some examples, computing device 2 may automatically send the image to a computer network accessed by trained medical professionals, instead of requiring the user to indicated sending the image. Any data input by the user may be saved in echo data 74 and associated with that patient. Patient information and images may be associated together and stored in echo data 74.

Image module 56 receives data from identification module 62 regarding the determination of what conditions, if any, are present. GUI 15 may include a user interface that allows user 2 to interact with computing device 10. GUI 15 may include graphical content, such as text, images, videos or any other visually displayable graphic object. User 2 may interact with GUI 15 to send the data to a medical network. Image module 56 may receive data from echo data 74 regarding layout format for the determined graphical content of the image and determined conditions or abnormalities. For example, if echo application is set in a first mode, then image module 56 may only display the image and an indication if there is an abnormality/condition with the option to send the data to an associated medical network. In a second module, image module 56 may include the option to review the condition indicators, for example with the highest probability. A user may select to view the indicators, causing image module 56 to include them in the display of the graphical element at output device 46 (e.g., presence-sensitive screen 72).

In some examples, image module 56 may use user gestures to determine the display of content. In this example, UI device 4 may detect a touch gesture (e.g., a tap, a swipe, etc.

by the user) at a location of UI device 4 that displays filtered content or an indication to show the filtered content. UI device 4 may detect the touch gesture and, in response, a UI module 6 (for example in data 48) may determine whether the touch gesture is at a location associated with one of the graphical buttons indicating to display the filtered content. When the touch gesture is within a specific location or predetermined distance of one of the identified displays, UI module 6 may cause UI device 4 to execute a change in the display of the graphical display, and in some instances, update the weighted probabilities associated with the displayed object in a specific application. Echo data 74 may store user input data and update weighted probabilities associated with an indicator or a condition.

User input data may be used to produce a graphical element that may be presented to the user (e.g., graphical elements may be displayed on screen, audio, and multimedia) or sent to an interface module (e.g., network interface, user interface, sensor module or another appropriate control module). In an embodiment, the processor module may be implemented as a single chip or multiple chips that may include plurality of digital and analogue processors. Computing device 2 may include UI module 52, image module 56, scan module 58, and identification module 62. Modules 52, 56, and 58 may perform operations described herein using software, hardware, or a mixture of both hardware and software residing in and executing on computing device 2. Computing device 2 may execute modules 52, 56 and 58 with multiple processors. Data received by computing device 2 or determined by any of the modules of computing device 2 may be stored in storage device(s) 48, such as image 70, condition 72, and echo data 74. Any user input or received network data may also be stored in the respective data store 70, 72, and 74, in addition to the echo image, or reimage, may also be stored in associated with other data, such as patient information.

Techniques of this disclosure may provide one or more advantages. For example, by automatically identifying heart condition indicators and suggesting/identifying possible heart conditions associated with the indicators, techniques of this disclosure may reduce the amount of time required to read an echo and diagnose heart conditions. Techniques of this disclosure may improve indicator identification and condition determination by "learning" conditions associated with indicators over time, e.g., by analyzing the context of the indicators associated with conditions and previous conditions selections. By reducing the need for finding indicators in an image initially presented to a user during image acquisition and by intelligently selecting a potential heart condition to suggest to the user, techniques of this disclosure may provide a better user experience and may reduce the time and effort required by the user to read an echo image.

Figure 3:
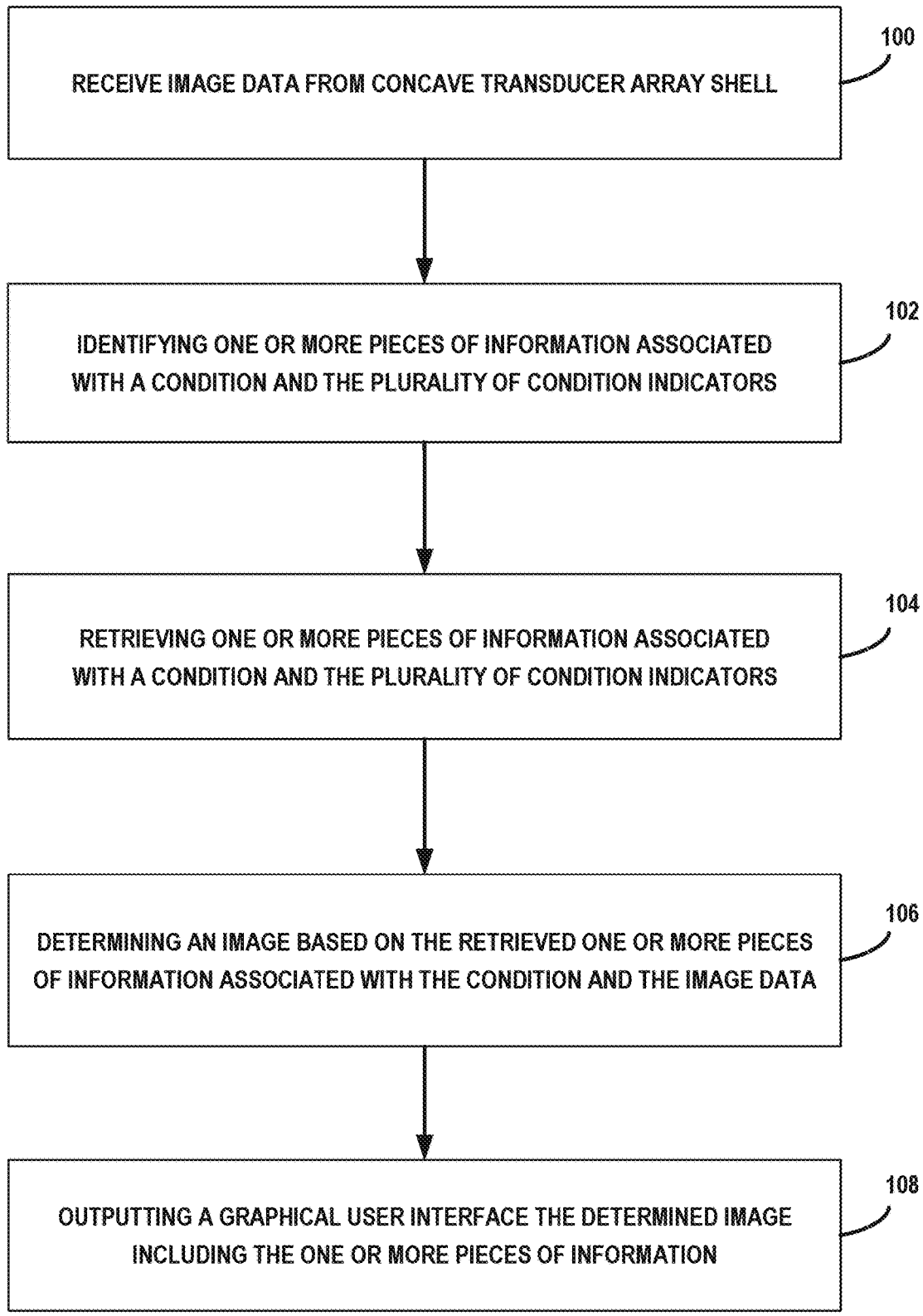
FIG. 3 is a flowchart illustrating an example process for using transducer array data for heart condition diagnosis, in accordance with one or more aspects of the present disclosure.

FIG. 3 is a flowchart illustrating an example process for using transducer array data for heart condition diagnosis, in accordance with one or more aspects of the present disclosure. Transducer array shell may receive an indication to begin scanning. The piezoelectric crystal arrays, once receiving signal, begin sending and receiving waves. The received waves at transmitted to the computing device. The sent signal information is the return wave that is the basis for the echo image, where the densities of the body return, or reflect, the signal differently, determining the image. Additional information may also be sent, such as location of the transducer crystals. Each crystal of each of the transducer arrays send and receives a signal, and then sending the plurality of received signals on to the computing device. Once the computing device receives the return signals, also known as image data, from the transducer arrays mounted to the semi-rigid concave inner side of the transducer portion (100), then the computing device may begin processing the signal and any other data to determine an image the newborn baby that is the subject of imaging. Computing device take the image, or the data that is the image basis, and compare the data to stored data. The stored data may include a number of different indicators associated with a condition the indicator are various pieces of information that may indicate a condition, such as thickening widths, irregular shapes, holes, volumes of blood, pumping pressure, rate of heart beat, etc., all of which may be signs or indications of cardiac problems. The computing device may identify similar pieces of information that may be in the received data that may be indicators of cardiac problems or abnormalities (102). The echo application may access the stored data that includes a listing of one or more pieces of information associated with a condition and the plurality of condition indicators (104). Stored data may also include user preferences and running the echo application in a first or second mode, depending on the level of skill and knowledge of the user. The pieces of information that are stored may also be received from a remote network that has updated condition information, population information, geographic information, family medical history, etc., all of which may be used in analysis and determination of a cardiac condition. In some instances, the echo application may apply a weighted probability scoring technique to determine likelihood of the received data matching the stored list of conditions indicators, and the application may also use a weighted probability technique to determine if the received indicators likely indicate a condition associated with the indicators (104). Other known matching and object identification techniques may also be applied to determine the presence of a condition. The echo application may also determine an image based on the received image data and other data and determine a graphical element that represents the received data. The graphical element may include some of the pieces of information associated with the condition when it is part of the view and the physical anatomy of the heart, but in other examples, the graphical element does not include some pieces of information, such as blood pressure or heart rate (106). The graphical element determined by the echo application may also access user preferences to determine layout style, such a s allowing the user to view the indicators determined and to view any determined cardiac condition or abnormality that matches the indicators from the scan (106). Is other examples, the image and associated data may be further sent to a medical network for further diagnosis or when there is an emergency, for immediate medical care. The computing device may take the information and output the graphical element at a graphical user interface. The GUI may show the image and some of the pieces of information, such as heart rate or measured distances/thicknesses (108). In some cases, the image quality may be poor or the data may be incomplete, so the computing device would cause the transducer array would rescan and the process would start over again.

Figure 4:
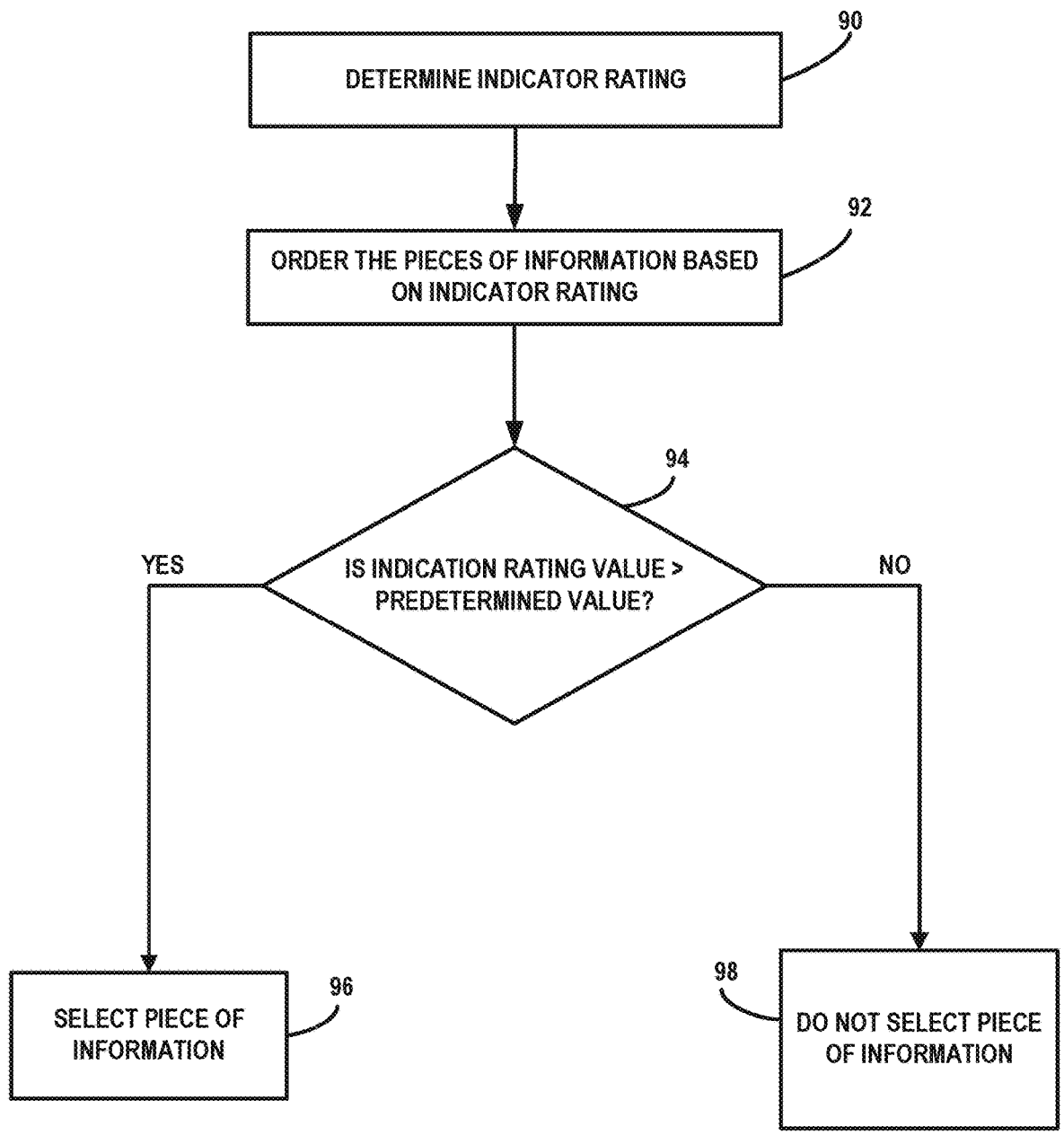
FIG. 4 is a flowchart illustrating an example process for using transducer array data for creating a graphical element in heart imaging and condition determination, in accordance with one or more aspects of the present disclosure.

FIG. 4 is a flowchart illustrating an example process for using transducer array data for creating a graphical element in heart imaging and condition determination, in accordance with one or more aspects of the present disclosure. The diagram illustrates a process of creating the image for the graphical element, and in some examples, for determining if a condition exists. After the array on the concave inner side transducer portion has sent the received signal data to the computing device, the echo application must use a process to sort through all of the information to determine which pieces of information may determine an image and which pieces of information may determine a cardiac condition. After identification of the pieces of information, particularly medical indicators of conditions and abnormalities, the echo application may determine an indicator rating of the weighted probability of a match with indicators associated with a cardiac condition(s) and stored in the computing device (90). The echo application may then order the pieces of information based on indicator rating (92). In some examples, the indications may have information that is weighted more heavily, and increasing the rating and ranking the information higher in the order. The echo application may apply a threshold value to determine which indicators are more likely to indicate that a condition is present in the new born being scanned. In some examples, the echo application may only use a percentage of the information, such as the top 3% of the information to determine a condition. The echo application may determine if the indication rating value is less than or more than a predetermined value (94). In some examples, the indication rating may be more than or equal to the threshold value (following the "Yes" branch). In this instance, the echo application selects the piece of information (96) and the piece of information may become part of the image. In some examples, the selected piece of information may be associated with a cardiac condition and the graphical element may include a notification of an association to a condition or abnormality. However, the ranking may be lower than the ranking. In some examples, when the indication rating is less than the threshold value (following the "No" branch), then the echo application may not select the piece of information (98). In this example, the piece of information may not be part of the graphical element created for outputting the image, and in some examples, it may not indicate a strong association to a condition, suggesting that the new born baby does not have a particular condition, or any condition from the plurality of stored conditions. The computing device may update the weighted probabilities with the ratings and values, storing them for future use by the echo application to determine. In some examples, the user may input information about the condition or the indications associated with conditions that may also update stored rankings for future matching and weighting.

Figure 5:
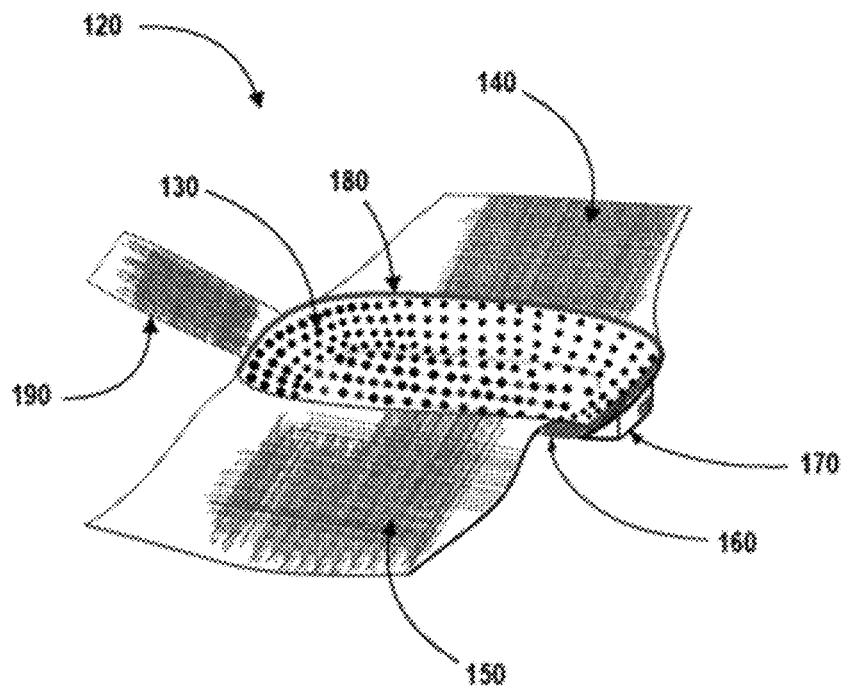
FIG. 5 is a conceptual diagram illustrating an example of a transducer array device used in echocardiograms.

FIG. 5 is a conceptual diagram illustrating an example of a transducer array device (120) used in echocardiograms. In some examples, the transducer portion (e.g., transducer portion 32 in FIG. 1) may have a curved shape and a concave inner side (180). The shape may be similar to a clam shell with at least the inner side (near or in contact with the newborn's skin) having a curved shape. The inner side is concave (180) allowing the transducer portion to lie in close contact to the skin of the newborn baby without much air in between causing the image quality to reduce. In some examples, the side of the transducer portion nearest to the newborn's anterior axillary line (or side 36) may also have a slight curve to conform to the curve of the rib cage under the left arm. In the example where the transducer portion curves on the axillary side, the transducer array crystals extend on the inner side, so that the area of received signals increases around the side of the body to image more of the heart. The transducer portion is made of a semi-rigid material that has little flexibility, and limiting movement of the transducer crystals. The concave inner side (180) may have transducers (130) mounted to the inner side. In some examples directly mounted or in other examples, the crystals (130) of the transducer arrays may be mounted to or secured by a mesh material that attaches to the concave inner side (not shown in FIG. 5) or attached, glued, secured, etc. to the inner side (180). The mesh secures the transducer crystals and limits their motion. Each crystal is connected to a wire (e.g., shown in FIG. 1). The wires may connect the crystals of a single array to the computing device (170), for individual array control or simultaneous array excitation. In other examples, the arrays may all connect to a single wire that connects to the connector unit and are powered and controlled simultaneously.

The design of the transducer portion shell is for a newborn baby, so the dimensions must accommodate a small thorax, allowing the transducer array to conform to a form fitting shape to the small body. For example, the transducer portion may have a width of 3 to 8 inches and a length of the newborn's rib cage, or the lower rib to the clavicle bone on the left anterior side, of 3 to 7 inches. The smaller the transducer portion, the lighter weight and less burdensome for breathing and improving comfort while wearing the device. Due to a shell shape, the width and length may be smaller initially and then get wider/longer in the middle and decrease again on the other side. Also contemplated in this disclosure is increasing the sizes to accommodate an adult for echo imaging. For example, the width for an adult would be 4 to 10 inches wide and 8 to 14 inches long.

The example illustration also shows a wrap that continues along the backside (160), which is opposite the concave inner side of the transducer portion. By extending the wrap material along the backside, the outer side, when the wrap is connected around the back on the posterior side of the patient, then the pulling or tight fit of the wrap will pull on the outer side of the transducer housing and cause the transducer portion to fit tightly against the skin of the newborn. Additionally, the wrap on the opposite outer side will limit the motion of the transducer array portion and hold it in place. In other examples, the wrap portion may have means fixing the wrap portion to the side of transducer housing on both sides of the transducer housing (e.g., 150 & 140). For example, the wrap may have a loop (such as a belt loop) that goes through a slit and wraps around a side piece to secure that side of the wrap portion. Each of the two sides may have a wrap portion extending from it (140 & 150), and in some cases, a wrap portion may extend from the clavicle side of transducer portion, for example at least one of second securing portion (190), that may extend around the shoulder of the newborn and attach to the other two side extending wrap portions (140 and 150) at the posterior side of the newborn. The wrap portion may connect or attach at the side of the newborn or posteriorly by Velcro, snaps, hooks, ties, or using other fixing techniques known. Velcro is a fastener made up of two strips of thin plastic sheet, one covered with tiny loops and the other with tiny flexible hooks, that adhere together when pressed together and separate when pulled apart.

For purposes of this disclosure the examples provided are for echo imaging for cardiac conditions or abnormalities. However, the echo may also be used in echo imaging of a newborn's lungs for conditions, such as pneumonia.

An ultrasound wrap for securing an array of piezoelectric transducers at a thoracic cavity anterior for echocardiology imaging, the ultrasound wrap comprising a transducer portion (also referred to as a transducer housing herein) having an array of piezoelectric transducers mounted to an inner concave surface of a semi-rigid structure, and at least one side securing portion extending from the transducer housing and comprising flexible material securely fitting around the thorax of a patient limiting the movement of the transducer housing. The ultrasound wrap may also include a first securing portion 140 that extends from at least one of the axillary sides of the transducer housing and configured to secure the transducer housing at the chest of the patient by securing the first securing portion 140 at least one of the posterior side of the newborn or the opposite axillary side of the transducer housing opposite the side that the first securing portion 140 extends from. The transducer housing may include a shoulder securing portion 190 that extends from a clavicle side of the transducer housing adjacent to the first axillary side, and the shoulder securing portion 190 may be secured at the posterior side of the patient. A second securing portion 150 may extend from the second axillary side of the transducer housing. The first securing portion connects to the second securing portion securely positioning the concave surface of the semi-rigid structure against the anterior side of the thoracic cavity, further wherein the first and second securing portions may securely connect at the posterior side of the thoracic cavity. The securing portions may be made of a flexible material comprises at least one of neoprene, gauze, cotton, polyester and rubber. The array of piezoelectric transducers is a linear array arranged linearly along to an array axis. The array of piezoelectric transducers comprising a plurality of ultrasound phased array transducers each comprising an array of transducer elements arranged linearly along an array axis, and each said phased array transducers having a filed view of about 90 degrees. The array of piezoelectric transducers may include more than one array group of piezoelectric transducers and each array group of piezoelectric transducers simultaneously receives power. The array of piezoelectric transducers configured to receive multiple signals for subaperture signal processing. The transducer portion may have a concave inner side in contact with the exterior thoracic cavity on the anterior side of the patient and the array of piezoelectric transducers is mounted to the concave inner side. The semi-rigid structure may include a material made of at least one of: polyethylene, polypropylene, vinyls, polyamides, polyesters, polyurethanes, polystyrene, copolymers, rubber, silicon, latex and thermosets. A flexible material that is in contact with the semi-rigid structure for securing the transducer portion to the anterior thoracic cavity reducing a gap between the transducer portion and the anterior thoracic cavity. The array of piezoelectric transducers may be fixed to a mesh material mounted upon the semi-rigid structure. The transducer portion may further have location elements for determining the position of the elements of the transducer arrays. The ultrasound wrap of claim 6, wherein an improved backing upon which the transducer elements and an electrode are mounted comprising rigid polymeric or polymer-coated particles fused into a macroscopically semi-rigid structure to provide high acoustic attenuation. The array of piezoelectric transducers contains more than one crystal, each crystal having a distance of 1-4 mm apart from another crystal of the array. The distance between crystals may be irregular and some areas of the array have a higher density of crystals. Each crystal of the array of piezoelectric crystals may have a uniform spacing from the other crystals of the array linearly align along an axis.

A method may comprise positioning an ultrasound wrap around the thoracic cavity of a patient for ultrasound imaging, wherein the ultrasound wrap comprises a transducer portion and a securing portion extending from the transducer portion, said transducer portion having an array of piezoelectric transducers mounted to a semi-rigid inner concave surface, positioning said transducer portion between the left clavicle and the bottom left rib at an anterior side of the thoracic cavity, positioning said securing portion around the anterior axillary line of the patient around to the posterior side of the patient, sending, by the array of piezoelectric transducers of the transducer portion, an ultrasound signal, receiving, by the transducer portion, a return signal that is an echo of the ultrasound signal, sending, from the transducer portion to a computing device, the return signal, and determining, by the computing device and based on the return signal and the ultrasound signal, an image for echocardiology and generating the image on a viewing device. The method may further comprise sending, by the transducer portion and to the computing device, an indication of the location of the location of each of the elements of the transducer array sensed by a sensor element on the transducer portion. In other examples, the method may further comprise positioning the securing portion of the ultrasound wrap clavicle side of the transducer portion at a posterior side of the thoracic cavity securely with substantially little space between the transducer portion and body tissue of the patient.

A system for automated ultrasound imaging may comprise a semi-rigid transducer portion having a concave inner side with piezoelectric transducer arrays thereon a computing device coupled to said transducer portion, where the computing device comprises a first database including a plurality of condition indicators associated with cardiac conditions a second database including ultrasound imaging settings, including user input, and a plurality of image data a processor configured to receive signals from the transducer arrays and control the transducer arrays for image acquisition image data associated with contextual identifiers from a transducer array and communicate with remote networks for sending acquired images. The system may further comprise a non-transitory computer readable medium encoded with instructions for the computing device coupled to said processor to control the piezoelectric transducer arrays for echo image acquisition compare the received image data with the plurality of condition indicators associated with cardiac conditions stored in the first database determine a cardiac condition based on the compared plurality of image data and the plurality of condition indicators associated with stored cardiac conditions, and generate a graphical element based on the determined cardiac condition.

Various embodiments have been described. These and other embodiments are within the copse of the following claims.

What is claimed is:

1. An ultrasound imaging device comprising:
  a rigid transducer housing having a longitudinal length and having a curved inner surface for placement about a body cavity of a patient for imaging, wherein the curved inner surface comprises a first curved surface side extending in a first direction and a second curved surface side extending in a second direction, the first direction being normal to the second direction, and a third curved surface side extending in a third direction opposite the first direction, the third curved surface side having a radius of curvature that is configured to extend around the left anterior axillary portion of the patient;
  an array of transducers coupled to the curved inner surface of the transducer housing;
  a shield layer disposed about the array of transducers;
  a computing device in communication with the transducers configured for processing transducer signals;
    wherein the computing device comprises at least one processor for signal processing transducer signals to generate image data and a database including a plurality of condition indicators associated with cardiac conditions, said computing device disposed about an external portion of the transducer housing and configured to compare the image data to the plurality of condition indicators; and a securing wrap configured to extend from the transducer housing to around at least part of the body cavity of a patient and to secure the transducer housing against the body cavity of the patient;

wherein the transducer housing further comprises a location sensor for determining a position of the elements of the transducer arrays.

2. The ultrasound imaging device of claim 1, wherein the securing wrap comprises a first securing portion extending from at least one side of the transducer housing extending around an axillary side of the patient, the wrap further comprising a second securing portion configured to extend at least around a shoulder of the patient for securing the transducer housing about the body cavity.

3. The ultrasound imaging device of claim 1, wherein the material of the securing wrap comprises at least one of neoprene, gauze, cotton, polyester or rubber.

4. The ultrasound imaging device of claim 1, wherein the array of transducers comprises a plurality of ultrasound phased array transducers each including an array of transducer elements arranged linearly along an array axis, and each said phased array transducers having a field of view within a range from 45 degrees to 120 degrees.

5. The ultrasound imaging device of claim 1, wherein the array of transducers comprises more than one array group of piezoelectric transducers and each array group of piezoelectric transducers simultaneously receives power.

6. The ultrasound imaging device of claim 5, wherein the curved inner surface comprises rigid polymeric or polymer-coated particles fused into a macroscopically semi-rigid structure wherein the array of transducers has a frequency between 1-10 MHz.

7. The ultrasound imaging device of claim 1, wherein the array of transducers is configured to receive multiple signals for subaperture signal processing.

8. The ultrasound imaging device of claim 1, wherein the transducer housing comprises at least one of: polyethylene, polypropylene, vinyls, polyamides, polyesters, polyurethanes, polystyrene, copolymers, rubber, silicone, latex, or thermosets.

9. The ultrasound imaging device of claim 1, wherein the array of transducers is disposed about a mesh material disposed about the transducer housing.

10. The ultrasound imaging device of claim 1, wherein the array of transducers contains more than one crystal, each crystal being disposed a distance of 1-4 mm apart from another crystal of the array.

11. The ultrasound imaging device of claim 1, wherein the array has a density of transducers on at least one portion of the array that is higher than other portions of the array.

12. The imaging device of claim 1, wherein the computing device is further configured to determine the weighted probability that at least one of the plurality of condition indicators corresponds to a likelihood of cardiac abnormality.

13. The imaging device of claim 12, wherein the computing device determines the weighted probability based on at least one of the geographic location, racial information, birth date, weight, height or other physical data.

14. An imaging device comprising:
a rigid transducer housing having a curved inner surface comprising a first curved inner surface side extending in a first direction and a second curved inner surface side extending in a second direction, the first direction being normal to the second direction;

an array of transducers coupled to the plurality of curved inner surfaces of the transducer housing;

wherein the first curved inner surface side of the transducer housing comprises a first radius of curvature and the second curved inner surface side of the transducer housing comprises a second radius of curvature, the first radius of curvature being different than the second radius of curvature; and a computing device in communication with the array of transducers, the computing device configured to acquire image data from the array of transducers, compare said image data to a plurality of condition indicators, and determine if a threshold for potential cardiac condition is met;

wherein the transducer housing comprises a length greater than its width;

wherein a portion of the curved inner surface is configured to extend around the left anterior axillary line of a patient;

wherein the rigid transducer housing is configured to position the array of transducers on the patient to produce consistent images without requiring a trained technician; and wherein the condition indicators comprise at least one of a thickness of heart ventricles, valve thickness, structural abnormalities of the heart, or blood flow.

15. The imaging device of claim 14, wherein first curved inner surface side has a width that is greater than a width of the second curved inner surface side.

16. The imaging device of claim 14, further comprising a third curved inner surface side extending in a direction opposite the first curved inner surface side and a fourth curved inner surface side extending in a direction opposite the second curved inner surface side.

17. An imaging device comprising:
an elongate rigid transducer housing having a curved inner surface with a plurality of curved inner surface sides, the plurality of curved inner surface sides comprising a first curved inner surface side extending in a first direction and a second curved inner surface side extending in a second direction, the first direction being normal to the second direction, wherein the transducer housing comprises a first section and a second section, each section comprising a width, wherein the width of the first section is smaller than the width of the second section;

wherein the first curved inner surface side is coupled to the first section of the transducer housing and the second curved inner surface side is coupled to the second section of the transducer housing;

a plurality of transducers coupled to the plurality of curved inner surfaces of the transducer housing, each one of the plurality of transducers being selectively operable to receive power individually or concurrently; and a computing device in communication with the plurality of transducers, said computing device comprising a first database including a plurality of condition indicators and a non-transitory computer readable medium encoded with instructions for the computing device to receive image data from the plurality of transducers, compare the received image data with the plurality of condition indicators, and determine a cardiac condition based on whether the compared image data and condition indicators exceed a pre-determined threshold value, wherein the first curved inner surface side of the transducer housing comprises a first radius of curvature and the second curved inner surface side of the transducer housing comprises a second radius of curvature, the first radius of curvature being different than the second radius of curvature, wherein the plurality of curved inner surface sides further comprises a third curved inner surface side extending in a third direction opposite the first direction, and wherein third curved surface side comprises a third radius of curvature, the third curved surface side configured to extend around the left anterior axillary portion of a patient.

18. The imaging device of claim 17, wherein the transducer housing comprises a third section having a width that is less than the second section.

19. The imaging device of claim 17, wherein the plurality of transducers are configured to be produce images of consistent quality without a hand-driven probe operated by a skilled user.

* * * * *